(12) United States Patent
Griscik et al.

(10) Patent No.: US 12,194,226 B2
(45) Date of Patent: *Jan. 14, 2025

(54) CAPSULES, HEAT-NOT-BURN (HNB) AEROSOL-GENERATING DEVICES, AND METHODS OF GENERATING AN AEROSOL

(71) Applicant: Altria Client Services LLC, Richmond, VA (US)

(72) Inventors: Gregory Griscik, Midlothian, VA (US); Thien Nguyen, Richmond, VA (US); Carl Kite, Midlothian, VA (US); David Alvarez, Richmond, VA (US); Terrance Bache, Richmond, VA (US); Zack Blackmon, Midlothian, VA (US); Patrick Good, Richmond, VA (US); Raymond Lau, Richmond, VA (US); Eric Hawes, Midlothian, VA (US); Cristian Popa, Hertfordshire (GB); James Yorkshades, Gamlingay (GB); Adam Parrott, Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 141 days.

This patent is subject to a terminal disclaimer.

(21) Appl. No.: 17/957,038

(22) Filed: Sep. 30, 2022

(65) Prior Publication Data

US 2023/0021933 A1 Jan. 26, 2023

Related U.S. Application Data

(63) Continuation of application No. 16/451,662, filed on Jun. 25, 2019, now Pat. No. 11,458,262.

(51) Int. Cl.
*A24F 47/00* (2020.01)
*A24F 40/42* (2020.01)
*A61M 11/04* (2006.01)

(52) U.S. Cl.
CPC ........... *A61M 11/042* (2014.02); *A24F 40/42* (2020.01)

(58) Field of Classification Search
CPC ........ A24F 40/42; A24F 40/46; A61M 11/042
See application file for complete search history.

(56) References Cited

U.S. PATENT DOCUMENTS

| 855,984 A | 6/1907 | Russell |
| 1,071,389 A | 8/1913 | Blosser |
| (Continued) | | |

FOREIGN PATENT DOCUMENTS

| CN | 203986136 U | 12/2014 |
| EP | 0525720 A1 | 2/1993 |
| (Continued) | | |

OTHER PUBLICATIONS

International Search Report and Written Opinion dated Oct. 8, 2020, issued in International Patent Application No. PCT/US2020/039085.

(Continued)

*Primary Examiner* — Eric Yaary
(74) *Attorney, Agent, or Firm* — Harness, Dickey & Pierce, P.L.C.

(57) ABSTRACT

A capsule for a heat-not-burn (HNB) aerosol-generating device may include a first frame, a second frame, a first heater, a second heater, and/or an aerosol-forming substrate. The first frame has a first interior face and a first exterior face. In addition, the first frame defines a first opening. The first heater may be secured to the first frame so as to cover the first opening. The second frame is connected to the first frame. The second frame has a second interior face and a second exterior face. Furthermore, the second frame defines a second opening. The second heater may be secured to the second frame so as to cover the second opening. The (Continued)

aerosol-forming substrate may be between the first heater and the second heater.

16 Claims, 34 Drawing Sheets

(56) References Cited

U.S. PATENT DOCUMENTS

| | | | |
|---|---|---|---|
| 1,934,887 A | 11/1933 | Robinson | |
| 4,214,146 A | 7/1980 | Schimanski | |
| 4,564,748 A | 1/1986 | Gupton | |
| 4,947,874 A | 8/1990 | Brooks et al. | |
| 5,388,572 A | 2/1995 | Mulhauser et al. | |
| 5,388,573 A | 2/1995 | Mulhauser et al. | |
| 5,441,060 A | 8/1995 | Rose et al. | |
| 5,460,173 A | 10/1995 | Mulhauser et al. | |
| 5,619,984 A | 4/1997 | Hodson et al. | |
| 5,645,050 A | 7/1997 | Zierenberg et al. | |
| 5,823,182 A | 10/1998 | Van Oort | |
| 6,006,747 A | 12/1999 | Eisele et al. | |
| 6,065,472 A | 5/2000 | Anderson et al. | |
| 6,095,153 A | 8/2000 | Kessler et al. | |
| 6,481,437 B1 | 11/2002 | Pate | |
| 7,186,958 B1 | 3/2007 | Nelson | |
| 7,997,280 B2 | 8/2011 | Rosenthal | |
| 8,488,952 B2 | 7/2013 | Landry | |
| 8,714,150 B2 | 5/2014 | Alelov | |
| 8,910,630 B2 | 12/2014 | Todd | |
| 2008/0073558 A1 | 3/2008 | Howell et al. | |
| 2010/0012118 A1 | 1/2010 | Storz | |
| 2010/0059070 A1 | 3/2010 | Potter et al. | |
| 2010/0313901 A1 | 12/2010 | Fernando et al. | |
| 2011/0126848 A1 | 6/2011 | Zuber et al. | |
| 2011/0192399 A1 | 8/2011 | Wilke et al. | |
| 2012/0304990 A1 | 12/2012 | Todd | |
| 2013/0233309 A1 | 9/2013 | Todd | |
| 2013/0233312 A1 | 9/2013 | Cohn | |
| 2013/0255702 A1 | 10/2013 | Griffith, Jr. et al. | |
| 2013/0276799 A1 | 10/2013 | Davidson et al. | |
| 2014/0060554 A1 | 3/2014 | Collett et al. | |
| 2014/0299141 A1 | 10/2014 | Flick | |
| 2014/0321837 A1 | 10/2014 | Flick | |
| 2014/0366609 A1 | 12/2014 | Beck et al. | |
| 2016/0021932 A1 | 1/2016 | Silvestrini et al. | |
| 2016/0057811 A1 | 2/2016 | Alarcon et al. | |
| 2016/0271347 A1 | 9/2016 | Raichman | |
| 2016/0331913 A1 | 11/2016 | Bourque | |
| 2016/0345629 A1 | 12/2016 | Mironov | |
| 2016/0366947 A1* | 12/2016 | Monsees | A24F 40/42 |
| 2017/0071251 A1 | 3/2017 | Goch | |
| 2017/0095624 A1* | 4/2017 | Davidson | A61P 29/00 |
| 2017/0164657 A1* | 6/2017 | Batista | A24F 40/42 |
| 2017/0196262 A1 | 7/2017 | Brereton et al. | |
| 2017/0340013 A1 | 11/2017 | Silvestrini et al. | |
| 2019/0200678 A1* | 7/2019 | Thorson | A24F 40/46 |
| 2020/0107585 A1* | 4/2020 | Atkins | H05B 3/42 |

FOREIGN PATENT DOCUMENTS

| | | |
|---|---|---|
| EP | 1007124 A1 | 6/2000 |
| EP | 1029451 A1 | 8/2000 |
| EP | 1385595 A2 | 2/2004 |
| EP | 1504768 A1 | 2/2005 |
| EP | 3989749 A1 | 5/2022 |
| JP | H10-056273 A | 2/1998 |
| JP | H10-238528 A | 9/1998 |
| JP | 2017-520263 A | 7/2017 |
| JP | 2017-523828 A | 8/2017 |
| WO | WO-2003/037306 A2 | 5/2003 |
| WO | WO-2015/116934 A1 | 8/2015 |
| WO | WO-2016/001921 A2 | 1/2016 |
| WO | WO-2016/001922 A1 | 1/2016 |
| WO | WO-2016/001923 A2 | 1/2016 |
| WO | WO-2016/001924 A2 | 1/2016 |
| WO | WO-2016/001925 A1 | 1/2016 |
| WO | WO-2016/001926 A1 | 1/2016 |
| WO | WO-2016/026219 A1 | 2/2016 |

OTHER PUBLICATIONS

International Preliminary Report on Patentability for PCT/US/2020/039085 dated Jan. 6, 2022.
Office Action dated Jun. 25, 2024 issued in Japanese Patent Application No. 2021-570812.
Office Action dated Oct. 8, 2024 issued in Mexican patent application No. MX/a/2021/014640.
Decision to Grant a Patent dated Nov. 19, 2024 issued in Japanese patent application No. 2021-570812.

* cited by examiner

640

642

2000

1410

1414  1416

CAPSULES, HEAT-NOT-BURN (HNB) AEROSOL-GENERATING DEVICES, AND METHODS OF GENERATING AN AEROSOL

CROSS-REFERENCE TO RELATED APPLICATION

This application is a continuation under 35 U.S.C. § 120 of U.S. application Ser. No. 16/451,662, filed on Jun. 25, 2019, the entire contents of which are hereby incorporated by reference.

BACKGROUND

Field

The present disclosure relates to capsules, heat-not-burn (HNB) aerosol-generating devices, and methods of generating an aerosol without involving a substantial pyrolysis of the aerosol-forming substrate.

Description of Related Art

Some electronic devices are configured to heat a plant material to a temperature that is sufficient to release constituents of the plant material while keeping the temperature below a combustion point of the plant material so as to avoid any substantial pyrolysis of the plant material. Such devices may be referred to as aerosol-generating devices (e.g., heat-not-burn aerosol-generating devices), and the plant material heated may be tobacco. In some instances, the plant material may be introduced directly into a heating chamber of an aerosol-generating device. In other instances, the plant material may be pre-packaged in individual containers to facilitate insertion and removal from an aerosol-generating device.

SUMMARY

At least one embodiment relates to a capsule for a heat-not-burn (HNB) aerosol-generating device. In an example embodiment, the capsule may include a first frame, a second frame, a first heater, a second heater, and/or an aerosol-forming substrate. The first frame has a first interior face and a first exterior face. In addition, the first frame defines a first opening. The first heater is secured to the first frame and covers the first opening. The second frame is connected to the first frame. The second frame has a second interior face and a second exterior face. Furthermore, the second frame defines a second opening. The second heater is secured to the second frame and covers the second opening. The aerosol-forming substrate may be between the first heater and the second heater.

At least one embodiment relates to a heat-not-burn (HNB) aerosol-generating device. In an example embodiment, the aerosol-generating device may include a device body, a plurality of electrodes, and a power source. The device body is configured to receive a capsule including a first frame, a second frame, a first heater, and/or a second heater. The plurality of electrodes are disposed within the device body and configured to electrically contact the first heater and/or the second heater of the capsule. The power source is configured to supply an electric current to the first heater and/or the second heater of the capsule via the plurality of electrodes.

At least one embodiment relates to a method of generating an aerosol. In an example embodiment, the method may include electrically contacting a plurality of electrodes with a capsule including a first frame, a second frame, a first heater, and/or a second heater. Additionally, the method may include supplying an electric current to the first heater and/or the second heater of the capsule via the plurality of electrodes.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

DETAILED DESCRIPTION

Figure 1:
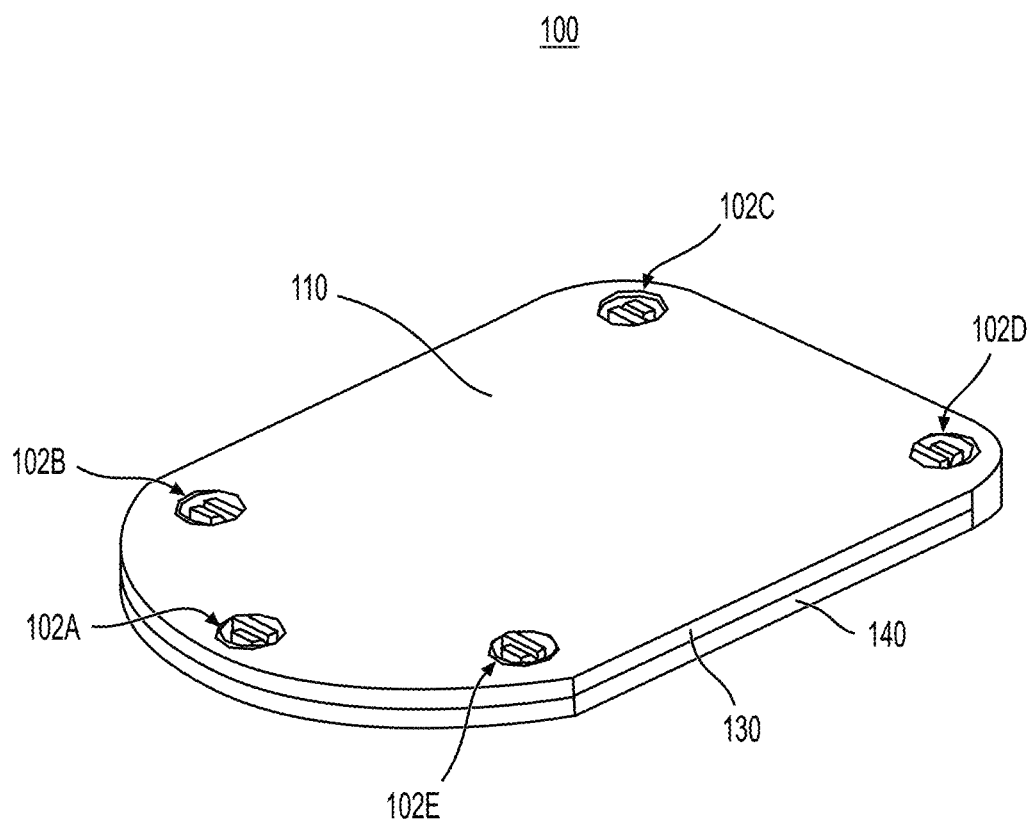
FIG. 1 is a perspective view of a first side of a capsule for an aerosol-generating device according to an example embodiment.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives thereof. Like numbers refer to like elements throughout the description of the figures.

It should be understood that when an element or layer is referred to as being "on," "connected to," "coupled to," "attached to," "adjacent to," or "covering" another element or layer, it may be directly on, connected to, coupled to, attached to, adjacent to or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations or sub-combinations of one or more of the associated listed items.

It should be understood that, although the terms first, second, third, etc. may be used herein to describe various elements, regions, layers and/or sections, these elements, regions, layers, and/or sections should not be limited by these terms. These terms are only used to distinguish one element, region, layer, or section from another region, layer, or section. Thus, a first element, region, layer, or section discussed below could be termed a second element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, and/or elements, but do not preclude the presence or addition of one or more other features, integers, steps, operations, elements, and/or groups thereof.

When the words "about" and "substantially" are used in this specification in connection with a numerical value, it is intended that the associated numerical value include a tolerance of ±10% around the stated numerical value, unless otherwise explicitly defined.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Hardware may be implemented using processing or control circuitry such as, but not limited to, one or more processors, one or more Central Processing Units (CPUs), one or more microcontrollers, one or more arithmetic logic units (ALUs), one or more digital signal processors (DSPs), one or more microcomputers, one or more field programmable gate arrays (FPGAs), one or more System-on-Chips (SoCs), one or more programmable logic units (PLUs), one or more microprocessors, one or more Application Specific Integrated Circuits (ASICs), or any other device or devices capable of responding to and executing instructions in a defined manner.

Figure 2:
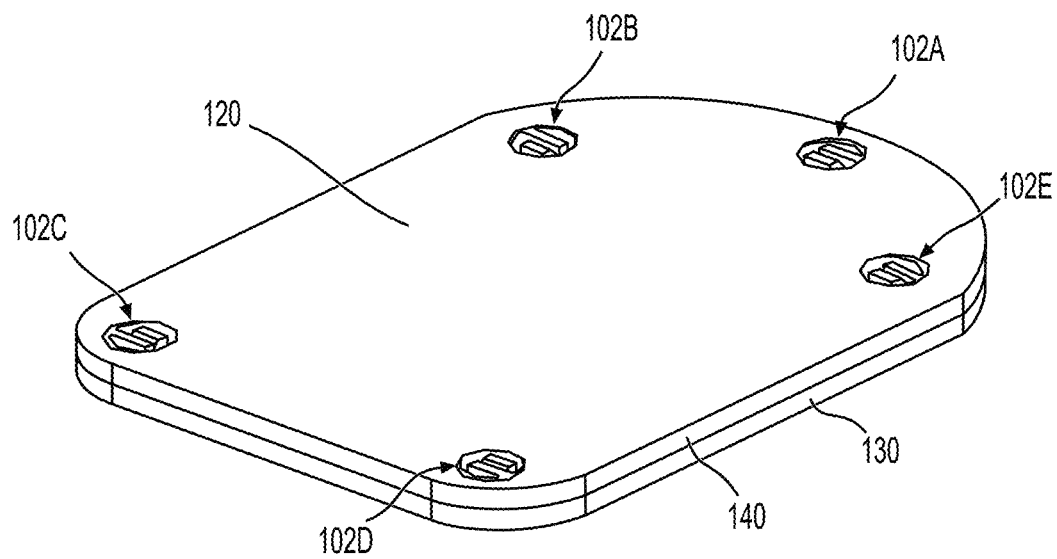
FIG. 2 is a perspective view of an opposing second side of the capsule of FIG. 1.

FIG. 1 is a perspective view of a first side of a capsule for an aerosol-generating device according to an example embodiment. FIG. 2 is a perspective view of an opposing second side of the capsule of FIG. 1. Referring to FIGS. 1-2, the capsule 100 may be configured to be received within an aerosol-generating device (e.g., heat-not-burn aerosol-generating device). In the drawings, the capsule 100 has a laminar structure and a planar form. The proximal end of the capsule 100 may have a curved proximal edge, and the opposing distal end may have a linear distal edge. In addition, a pair of linear side edges may connect the curved proximal edge and the linear distal edge. The pair of linear side edges may be parallel to each other. Furthermore, the junctions of the linear side edges with the linear distal edge may be in the form of rounded corners.

Although the capsule 100 is shown in the figures as resembling a rectangle with a semicircular end (e.g., elongated semicircle, semi-obround), it should be understood that other configurations may be employed. For instance, the shape may be circular such that the capsule 100 has a disk-like appearance. In another instance, the shape of the capsule 100 may be elliptical or racetrack-like. In other instances, the capsule 100 may have a polygonal shape (regular or irregular), including a triangle, a rectangle (e.g., square), a pentagon, a hexagon, a heptagon, or an octagon. The laminar structure and generally planar form of the capsule 100 may facilitate stacking so as to allow a plurality of capsules to be stored in an aerosol-generating device or other receptacle for dispensing a new capsule or receiving a depleted capsule.

The capsule 100 includes a first frame 130 and a second frame 140. The first frame 130 and the second frame 140 may be of the same shape and size and aligned such that the outer sidewalls are substantially flush with each other, although example embodiments are not limited thereto. The first frame 130 and the second frame 140 may be formed of a suitable polymer, such as polyether ether ketone (PEEK), liquid crystal polymer (LCP), and/or ultra-high molecular weight polyethylene (UHMWPE). The first frame 130 and the second frame 140 are connected via connections 102*a*, 102*b*, 102*c*, 102*d*, and 102*e*. While five connections are shown in the figures, it should be understood that more (e.g., seven) or less (e.g., three) connections may be utilized. Connections 102*a*, 102*b*, and 102*e* may be along the curved proximal edge of the proximal end, while connections 102*c* and 102*d* may be along the linear distal edge of the opposing distal end (e.g., adjacent to the rounded corners). Connection 102*a* may be equidistantly spaced from and more proximal than connections 102*b* and 102*e*. Additionally, the distance between connections 102*b* and 102*e* may be equal to the distance between connections 102*c* and 102*d*. Also, the distance between connections 102*b* and 102*c* may be equal to the distance between connections 102*e* and 102*d*. Connections 102*a*, 102*b*, 102*c*, 102*d*, and 102*e* will be discussed in further detail herein.

A first heater 110 is secured to the first frame 130, and a second heater 120 is secured to the second frame 140. The first frame 130 and the second frame 140 are non-conductive and electrically isolate the first heater 110 and the second heater 120. The capsule 100 is configured to hold an aerosol-forming substrate, which may be between the first heater 110 and the second heater 120. The first heater 110 and the second heater 120 are configured to heat the aerosol-forming substrate. As a result of the heating, the temperature of the aerosol-forming substrate may increase, and an aerosol may be generated. The first heater 110 and the second heater 120 may be in a form of a mesh, a perforated foil, or a combination thereof. For instance, both the first heater 110 and the second heater 120 may be in a form of a mesh. In another instance, both the first heater 110 and the second heater 120 may be in a form of a perforated foil (e.g., 80, 100, or 250 mesh equivalent). The perforated foil may be perforated mechanically or chemically (e.g., via photochemical machining/etching). In yet another instance, one of the first heater 110 or the second heater 120 may be in a form of a mesh, while the other of the first heater 110 or the second heater 120 may be in a form of a perforated foil. The first heater 110 and the second heater 120 (as well as the first frame 130 and the second frame 140) may be substantially the same size based on a plan view (e.g., ±10% of a given dimension).

As discussed herein, an aerosol-forming substrate is a material or combination of materials that may yield an aerosol. An aerosol relates to the matter generated or output by the devices disclosed, claimed, and equivalents thereof. The material may include a compound (e.g., nicotine, cannabinoid), wherein an aerosol including the compound is produced when the material is heated. The heating may be below the combustion temperature so as to produce an aerosol without involving a substantial pyrolysis of the aerosol-forming substrate or the substantial generation of combustion byproducts (if any). Thus, in an example embodiment, pyrolysis does not occur during the heating and resulting production of aerosol. In other instances, there may be some pyrolysis and combustion byproducts, but the extent may be considered relatively minor and/or merely incidental.

The aerosol-forming substrate may be a fibrous material. For instance, the fibrous material may be a botanical material. The fibrous material is configured to release a compound when heated. The compound may be a naturally occurring constituent of the fibrous material. For instance, the fibrous material may be plant material such as tobacco, and the compound released may be nicotine. The term "tobacco" includes any tobacco plant material including tobacco leaf, tobacco plug, reconstituted tobacco, compressed tobacco, shaped tobacco, or powder tobacco, and combinations thereof from one or more species of tobacco plants, such as *Nicotiana rustica* and *Nicotiana tabacum*.

In some example embodiments, the tobacco material may include material from any member of the genus *Nicotiana*. In addition, the tobacco material may include a blend of two or more different tobacco varieties. Examples of suitable types of tobacco materials that may be used include, but are not limited to, flue-cured tobacco, Burley tobacco, Dark tobacco, Maryland tobacco, Oriental tobacco, rare tobacco, specialty tobacco, blends thereof, and the like. The tobacco material may be provided in any suitable form, including, but not limited to, tobacco lamina, processed tobacco materials, such as volume expanded or puffed tobacco, processed tobacco stems, such as cut-rolled or cut-puffed stems, reconstituted tobacco materials, blends thereof, and the like. In some example embodiments, the tobacco material is in the form of a substantially dry tobacco mass. Furthermore, in some instances, the tobacco material may be mixed and/or combined with at least one of propylene glycol, glycerin, sub-combinations thereof, or combinations thereof.

The compound may also be a naturally occurring constituent of a medicinal plant that has a medically-accepted therapeutic effect. For instance, the medicinal plant may be a *Cannabis* plant, and the compound may be a cannabinoid. Cannabinoids interact with receptors in the body to produce a wide range of effects. As a result, cannabinoids have been used for a variety of medicinal purposes (e.g., treatment of pain, nausea, epilepsy, psychiatric disorders). The fibrous material may include the leaf and/or flower material from one or more species of *Cannabis* plants such as *Cannabis sativa*, *Cannabis indica*, and *Cannabis ruderalis*. In some instances, the fibrous material is a mixture of 60-80% (e.g., 70%) *Cannabis sativa* and 20-40% (e.g., 30%) *Cannabis indica*.

Examples of cannabinoids include tetrahydrocannabinolic acid (THCA), tetrahydrocannabinol (THC), cannabidiolic acid (CBDA), cannabidiol (CBD), cannabinol (CBN), cannabicyclol (CBL), cannabichromene (CBC), and cannabigerol (CBG). Tetrahydrocannabinolic acid (TI-ICA) is a precursor of tetrahydrocannabinol (THC), while cannabidiolic acid (CBDA) is precursor of cannabidiol (CBD). Tetrahydrocannabinolic acid (THCA) and cannabidiolic acid (CBDA) may be converted to tetrahydrocannabinol (TI-IC) and cannabidiol (CBD), respectively, via heating. In an example embodiment, heat from the first heater 110 and/or the second heater 120 may cause decarboxylation so as to convert the tetrahydrocannabinolic acid (THCA) in the capsule 100 to tetrahydrocannabinol (THC), and/or to convert the cannabidiolic acid (CBDA) in the capsule 100 to cannabidiol (CBD).

In instances where both tetrahydrocannabinolic acid (THCA) and tetrahydrocannabinol (THC) are present in the capsule 100, the decarboxylation and resulting conversion will cause a decrease in tetrahydrocannabinolic acid (THCA) and an increase in tetrahydrocannabinol (THC). At least 50% (e.g., at least 87%) of the tetrahydrocannabinolic acid (THCA) may be converted to tetrahydrocannabinol (THC) during the heating of the capsule 100. Similarly, in instances where both cannabidiolic acid (CBDA) and cannabidiol (CBD) are present in the capsule 100, the decarboxylation and resulting conversion will cause a decrease in cannabidiolic acid (CBDA) and an increase in cannabidiol (CBD). At least 50% (e.g., at least 87%) of the cannabidiolic add (CBDA) may be converted to cannabidiol (CBD) during the heating of the capsule 100.

Furthermore, the compound may be or may additionally include a non-naturally occurring additive that is subsequently introduced into the fibrous material. In one instance, the fibrous material may include at least one of cotton, polyethylene, polyester, rayon, combinations thereof, or the like (e.g., in a form of a gauze). In another instance, the fibrous material may be a cellulose material (e.g., non-tobacco and/or non-cannabis material). In either instance, the compound introduced may include nicotine, cannabinoids, and/or flavorants. The flavorants may be from natural sources, such as plant extracts (e.g., tobacco extract, *Cannabis* extract), and/or artificial sources. In yet another instance, when the fibrous material includes tobacco and/or *Cannabis*, the compound may be or may additionally include one or more flavorants (e.g., menthol, mint, vanilla). Thus, the compound within the aerosol-forming substrate may include naturally occurring constituents and/or non-naturally occurring additives. In this regard, it should be understood that existing levels of the naturally occurring constituents of the aerosol-forming substrate may be increased through supplementation. For example, the existing levels of nicotine in a quantity of tobacco may be increased through supplementation with an extract containing nicotine. Similarly, the existing levels of one or more cannabinoids in a quantity of *Cannabis* may be increased through supplementation with an extract containing such cannabinoids.

In an example embodiment, the first heater 110 and the second heater 120 are configured to undergo Joule heating (which is also known as ohmic/resistive heating) upon the application of an electric current thereto. Stated in more detail, the first heater 110 and the second heater 120 may be formed of conductors (same or different) and configured to produce heat when an electric current passes through the conductors. The electric current may be supplied from a power source (e.g., battery) within the aerosol-generating device. Suitable conductors for the first heater 110 and the second heater 120 include an iron-based alloy (e.g., stainless steel) and/or a nickel-based alloy (e.g., nichrome). The first heater 110 and the second heater 120 may have a thickness of about 0.0010 inch or less (e.g., 0.0005 inch) and a resistance of about 0.15-0.5 Ohm. Furthermore, although both the first heater 110 and the second heater 120 are shown in FIGS. 1-2, it should be understood that, in some example embodiments, only one of the first heater 110 or the second heater 120 is needed.

The electric current from the power source may be transmitted via electrodes configured to electrically contact the first heater 110 and the second heater 120 when the capsule 100 is inserted into the aerosol-generating device. In a non-limiting embodiment, the electrodes may be spring-loaded to enhance an engagement with the first heater 110 and the second heater 120 of the capsule 100. Also, the movement (e.g., engagement, release) of the electrodes may be achieved by mechanical actuation. The electrodes will be discussed in further detail herein. Furthermore, the supply of the electric current from the aerosol-generating device to the capsule 100 may be a manual operation (e.g., button-activated) or an automatic operation (e.g., puff-activated).

Figure 3:
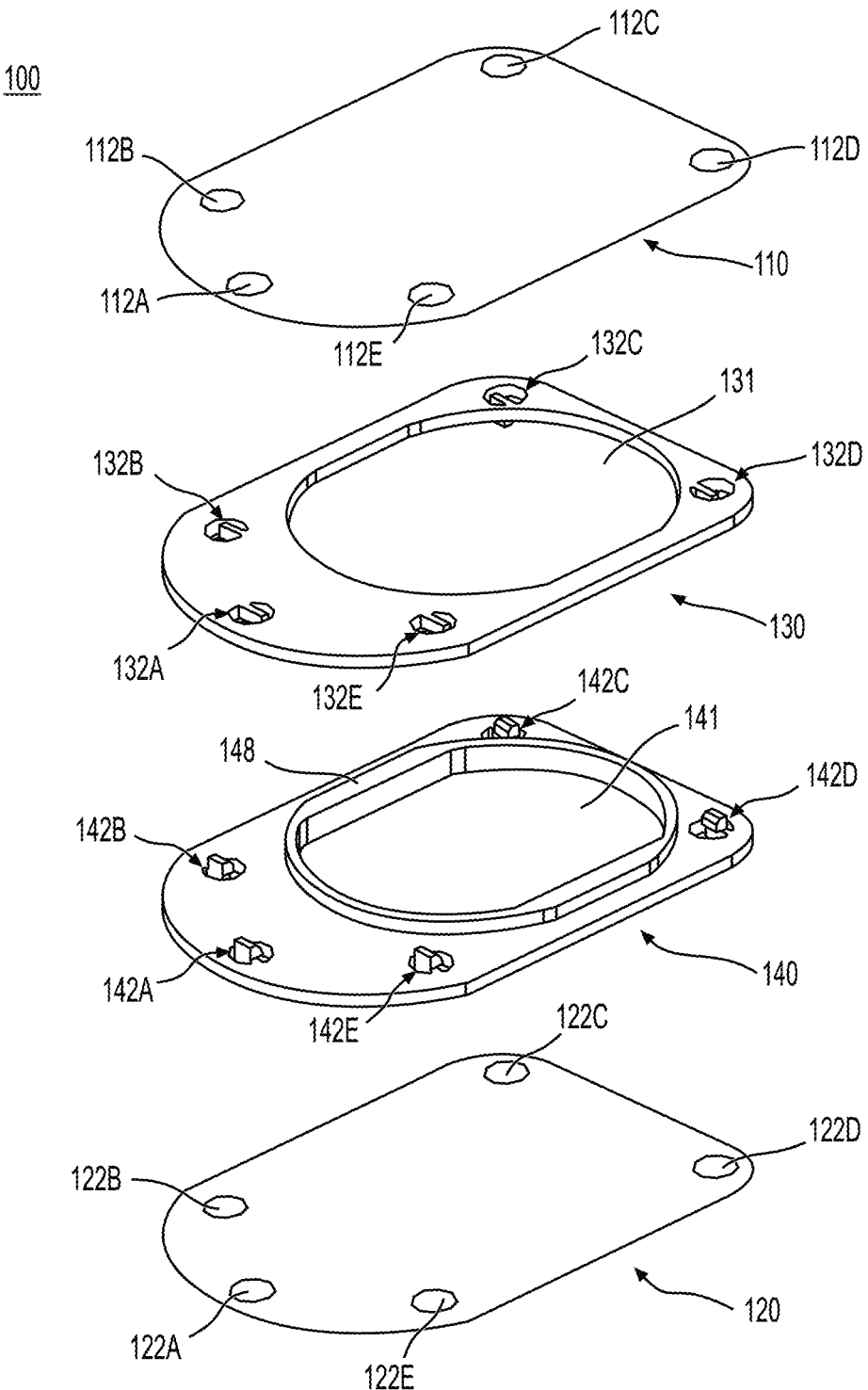
FIG. 3 is an exploded view of the capsule of FIG. 1.
Figure 4:
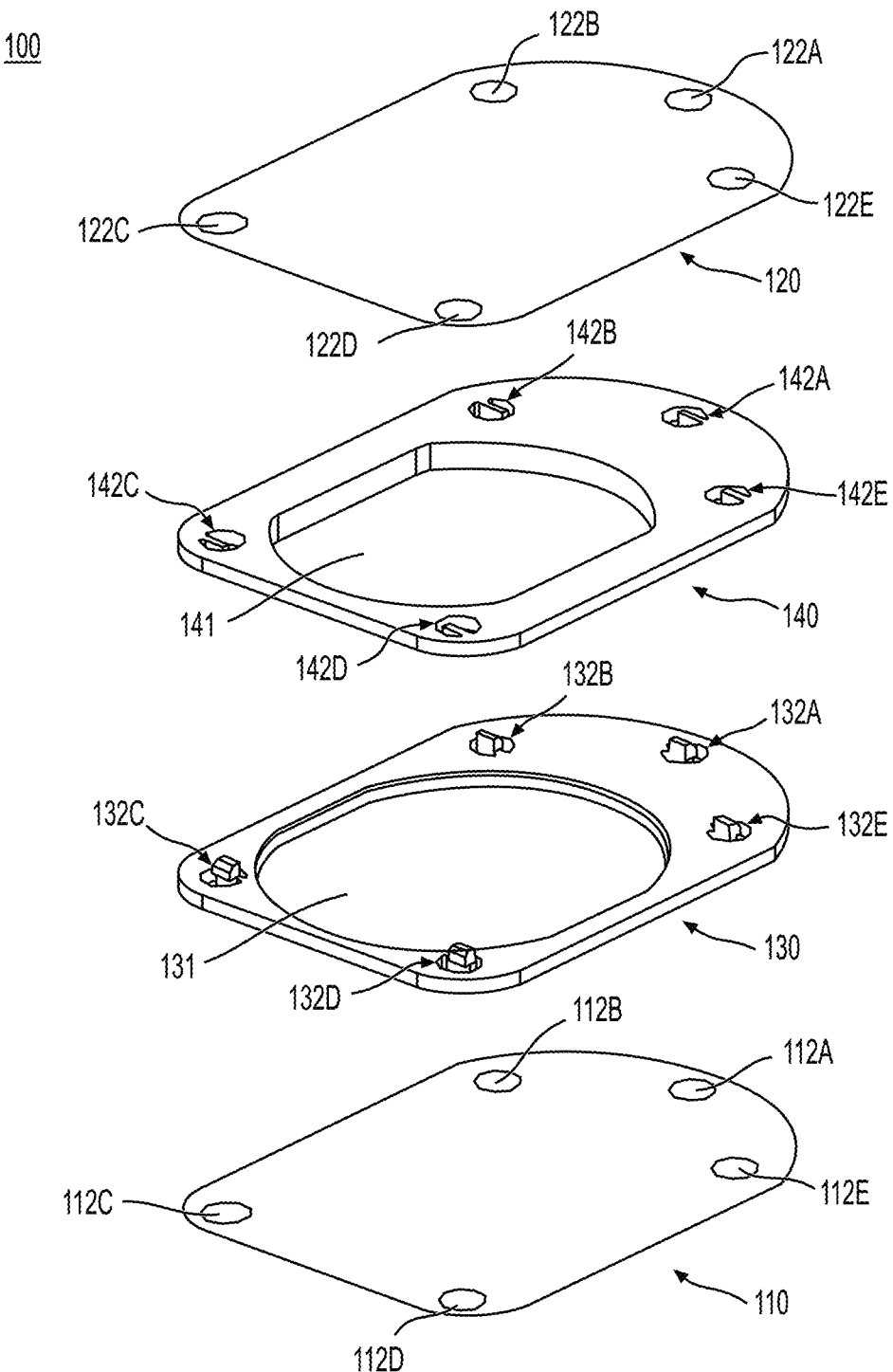
FIG. 4 is an exploded view of the capsule of FIG. 2.

FIG. 3 is an exploded view of the capsule of FIG. 1. FIG. 4 is an exploded view of the capsule of FIG. 2. Referring to FIGS. 3-4, the first frame 130 has a first interior face and a first exterior face. In addition, the first frame 130 defines an opening 131 (e.g., first opening). In an example embodiment, the sidewall of the opening 131 has opposing linear sections and opposing curved sections, wherein one curved section is adjacent to first connectors 132a, 132b, and 132e, and the other curved section is adjacent to first connectors 132c and 132d. The first heater 110 is secured to the first exterior face of the first frame 130 and covers the opening 131. Furthermore, the first heater 110 defines first apertures 112a, 112b, 112c, 112d, and 112e. The first apertures 112a, 112b, 112c, 112d, and 112e may be positioned and sized so as to expose the first connectors 132a, 132b, 132c, 132d, and 132e, respectively, when the first heater 110 is secured to the first frame 130.

The second frame 140 has a second interior face and a second exterior face. In addition, the second frame 140 defines an opening (e.g., second opening). The second frame 140 also includes a rim 148 around the opening so as to define a cavity 141 configured to receive an aerosol-forming substrate. As shown in the figures, the inner sidewall of the rim 148 may be even with the inner sidewall of the opening in the second frame 140 so as to form a single inner sidewall. In an example embodiment, the inner sidewall of the cavity 141 has opposing linear sections and opposing curved sections, wherein one curved section is adjacent to second connectors 142a, 142b, and 142e, and the other curved section is adjacent to second connectors 142c and 142d. The second heater 120 is secured to the second exterior face of the second frame 140 and covers the cavity 141. Furthermore, the second heater 120 defines second apertures 122a, 122b, 122c, 122d, and 122e. The second apertures 122a, 122b, 122c, 122d, and 122e may be positioned and sized so as to expose the second connectors 142a, 142b, 142c, 142d, and 142e, respectively, when the second heater 120 is secured to the second frame 140.

The first heater 110 and the second heater 120 may be secured to the first frame 130 and the second frame 140, respectively, via a variety of attachment techniques. For instance, the attachment technique may involve injection molding (e.g., insert molding, over molding). In another instance, the attachment technique may involve ultrasonic welding. In other instances, the attachment technique may involve an adhesive (e.g., tape, glue) that has been deemed food-safe or otherwise acceptable by a regulatory authority.

During assembly, the first frame 130 may be connected to the second frame 140 after an aerosol-forming substrate is disposed within the cavity 141. In an example embodiment, the rim 148 of the second frame 140 will be seated within the opening 131 of the first frame 130 as part of such a connection. For instance, the outer sidewall of the rim 148 may engage with the sidewall of the opening 131 in the first frame 130. Such an engagement may be via an interference fit (which may also be referred to as a press fit or friction fit).

Alternatively, there may be a clearance between the rim 148 and the opening 131 so as to allow a relatively small degree of freedom between the second frame 140 and the first frame 130 (e.g., rotation of about ±10° or less).

The first frame 130 includes at least one first connector protruding from the first interior face of the first frame 130. The at least one first connector of the first frame 130 may be in a form of first connectors 132a, 132b, 132c, 132d, and 132e. Similarly, the second frame 140 includes at least one second connector protruding from the second interior face of the second frame 140. The at least one second connector of the second frame 140 may be in a form of second connectors 142a, 142b, 142c, 142d, and 142e. The at least one first connector of the first frame 130 is configured to engage with the at least one second connector of the second frame 140 to form at least one connection such that the first interior face of the first frame 130 is adjacent to the second interior face of the second frame 140. The at least one connection of the capsule 100 may be in a form of connections 102a, 102b, 102c, 102d, and 102e.

Figure 5:
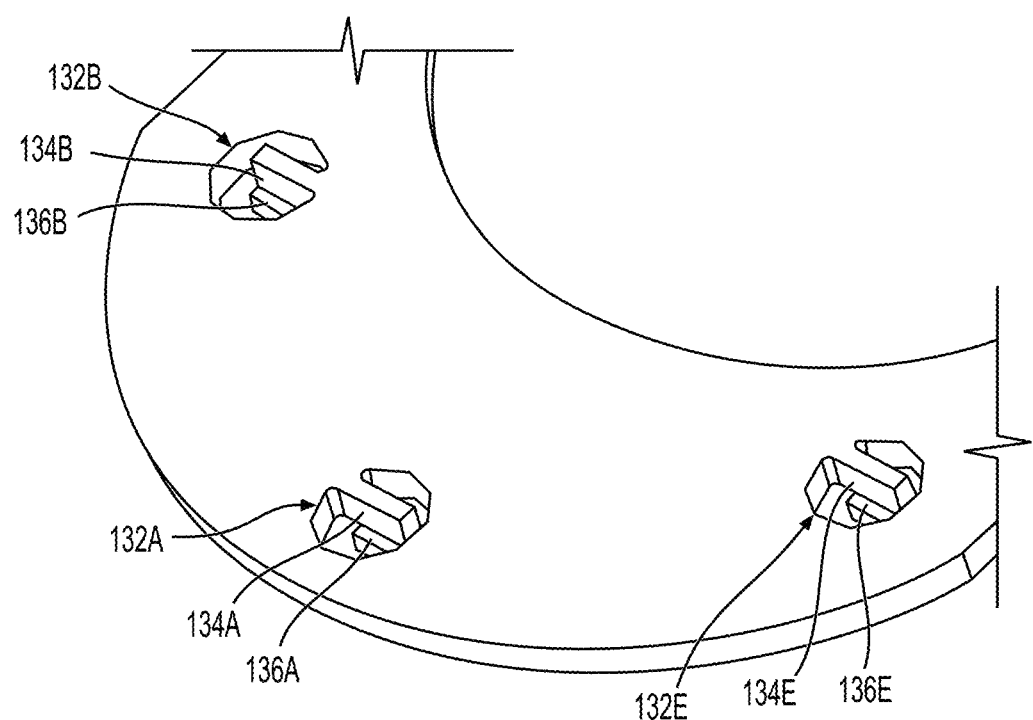
FIG. 5 is an enlarged view of the first connectors of the first frame of FIG. 3.

FIG. 5 is an enlarged view of the first connectors of the first frame of FIG. 3. Referring to FIG. 5, each of the first connectors (e.g., first connector 132a) of the first frame 130 includes a first arm portion (e.g., first arm portion 134a) and a first catch portion (e.g., first catch portion 136a). The first arm portion may be coplanar with the first frame 130. The first catch portion may protrude from the first interior face of the first frame 130. In an example embodiment, the first connectors may be parts of the first frame 130 where first arm portions (together with their respective first catch portions) extend into corresponding first orifices defined by the first frame 130. In such an instance, the first arm portions and the first catch portions of the first connectors may be regarded as being integrally formed with the first frame 130. As shown and discussed in further detail, the first connectors 132a, 132b, and 132e include first arm portions 134a, 134b, and 134e, respectively, extending into corresponding first orifices defined by the first frame 130. In addition, the first connectors 132a, 132b, and 132e include first catch portions 136a, 136b, and 136e, respectively, protruding from the first interior face of the first frame 130. Furthermore, the first catch portions 136a, 136b, and 136e may extend orthogonally relative to the first arm portions 134a, 134b, and 134e, respectively, so as to form corresponding first ledges.

Figure 6:
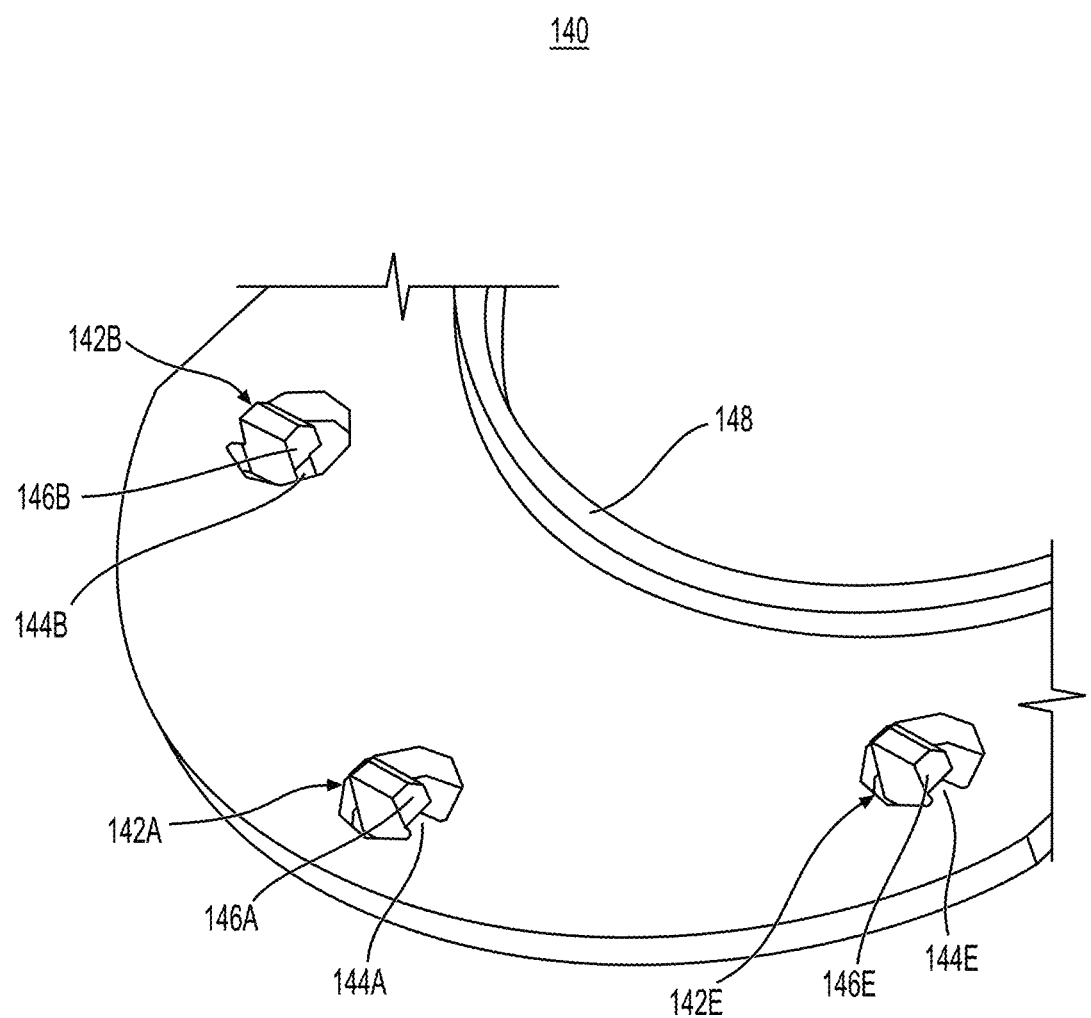
FIG. 6 is an enlarged view of the second connectors of the second frame of FIG. 3.

FIG. 6 is an enlarged view of the second connectors of the second frame of FIG. 3. Referring to FIG. 6, each of the second connectors (e.g., second connector 142a) of the second frame 140 includes a second arm portion (e.g., second arm portion 144a) and a second catch portion (e.g., second catch portion 146a). The second arm portion may be coplanar with the second frame 140. The second catch portion may protrude from the second interior face of the second frame 140. In an example embodiment, the second connectors may be parts of the second frame 140 where second arm portions (together with their respective second catch portions) extend into corresponding second orifices defined by the second frame 140. In such an instance, the second arm portions and the second catch portions of the second connectors may be regarded as being integrally formed with the second frame 140. As shown and discussed in further detail, the second connectors 142a, 142b, and 142e include second arm portions 144a, 144b, and 144e, respectively, extending into corresponding second orifices defined by the second frame 140. In addition, the second connectors 142a, 142b, and 142e include second catch portions 146a, 146b, and 146e, respectively, protruding from the second interior face of the second frame 140. Furthermore, the second catch portions 146a, 146b, and 146e may extend orthogonally relative to the second arm portions 144a, 144b, and 144e, respectively, so as to form corresponding second ledges.

Figure 7:
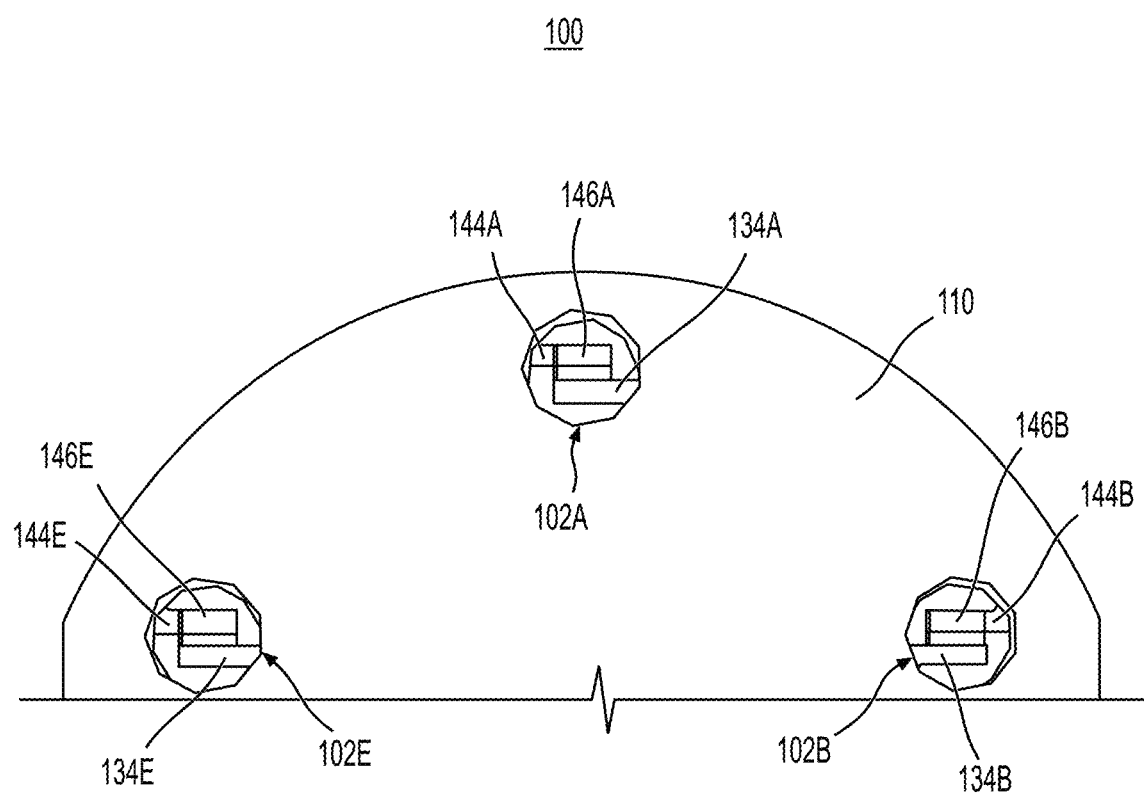
FIG. 7 is a plan view of the connections of FIG. 1.

FIG. 7 is a plan view of the connections of FIG. 1. Referring to FIG. 7, the first frame 130 and the second frame 140 are connected via a plurality of connections (e.g., connection 102a) during the assembly of the capsule 100. In an example embodiment, the at least one first connector of the first frame 130 is configured to be in an interlocking arrangement with the at least one second connector of the second frame 140 to form such connections (e.g., internal snap connections). For instance, as shown, the first catch portion 136a of the first connector 132a is configured to engage with the second catch portion 146a of the second connector 142a to form a connection 102a. Similarly, the first catch portion 136b of the first connector 132b is configured to engage with the second catch portion 146b of the second connector 142b to form a connection 102b. Also shown, the first catch portion 136e of the first connector 132e is configured to engage with the second catch portion 146e of the second connector 142e to form a connection 102e.

During the formation of the connections 102a, 102b, and 102e in FIG. 7, the first arm portions 134a, 134b, and 134e and the second arm portions 144a, 144b, and 144e may deflect with respect to each other so as to allow the first catch portions 136a, 136b, and 136e and the second catch portions 146a, 146b, and 146e to resiliently slip past each other before springing back, thereby allowing the first ledges of the first connectors 132a, 132b, and 132e to interlock or otherwise interface with the second ledges of the second connectors 142a, 142b, and 142e. In such an instance, the first catch portions 136a, 136b, and 136e may extend into the second orifices defined by the second frame 140, while the second catch portions 146a, 146b, and 146e may extend into the first orifices defined by the first frame 130.

In a non-limiting embodiment, the height (e.g., degree of protrusion) of the first catch portions 136a, 136b, and 136e may be equal to or less than the thickness of the second frame 140 such that the first catch portions 136a, 136b, and 136e do not extend beyond the second exterior face of the second frame 140. Similarly, the height (e.g., degree of protrusion) of the second catch portions 146a, 146b, and 146e may be equal to or less than the thickness of the first frame 130 such that the second catch portions 146a, 146b, and 146e do not extend beyond the first exterior face of the first frame 130. Furthermore, when in an interlocking arrangement, the first arm portions 134a, 134b, and 134e may be parallel to the second arm portions 144a, 144b, and 144e, respectively, although example embodiments are not limited thereto. While the above discussion involves the connections 102a, 102b, and 102e shown in FIG. 7, it should be understood that this description also applies to the other connections (e.g., connections 102c and 102d) shown in FIG. 1. Once assembled, the capsule 100 is difficult or impracticable to open without damaging the connectors, the frames, and/or other aspects of the capsule 100. As a result, the capsule 100 is relatively tamper-proof against unauthorized actions by third parties.

The capsule 100 has been described as including, inter alia, a first frame 130 that is separate from a second frame 140. Alternatively, in some instances, the first frame 130 and the second frame 140 may be fabricated as a single structure that is configured to fold during assembly such that the first connectors (e.g., first connector 132a) engage with the second connectors (e.g. second connector 142a). For example, the first frame 130 and the second frame 140 may resemble a clamshell structure, wherein the linear distal edge of the first frame 130 is connected to the linear distal edge of the second frame 140 with an integral section of reduced thickness that functions as a fold line. In another example, a linear side edge of the first frame 130 may be connected to a linear side edge of the second frame 140 with an integral section of reduced thickness that functions as a fold line. With a clamshell structure, it should be understood that one or more connections (e.g., connections 102b, 102c, and/or 102d) may be omitted from the capsule 100.

Figure 8:
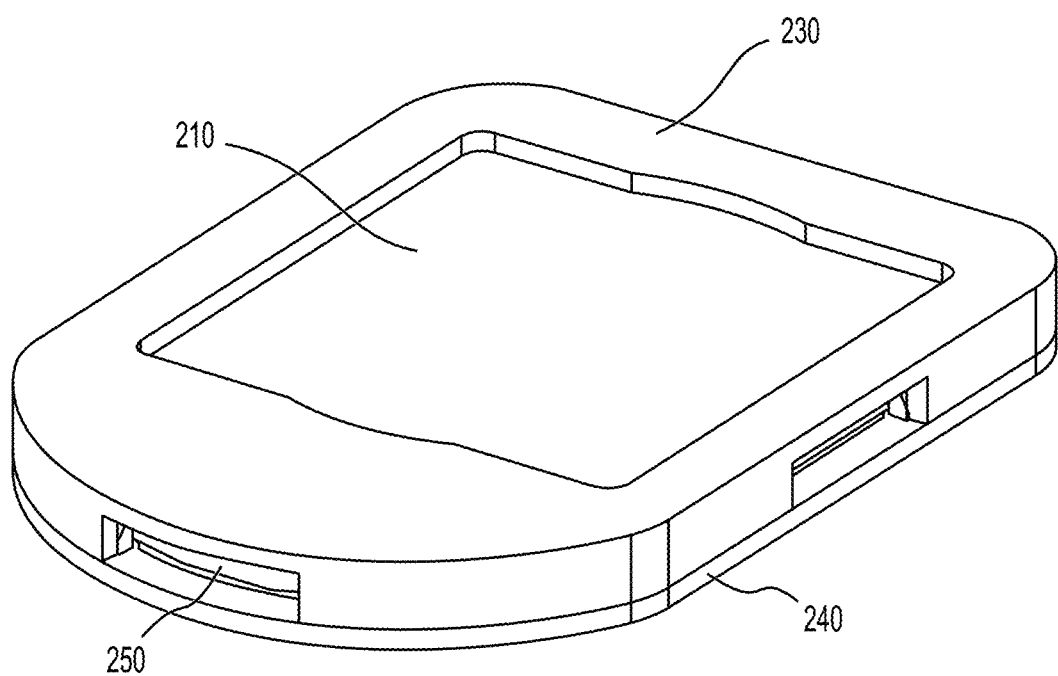
FIG. 8 is a perspective view of a first side of another capsule for an aerosol-generating device according to an example embodiment.
Figure 9:
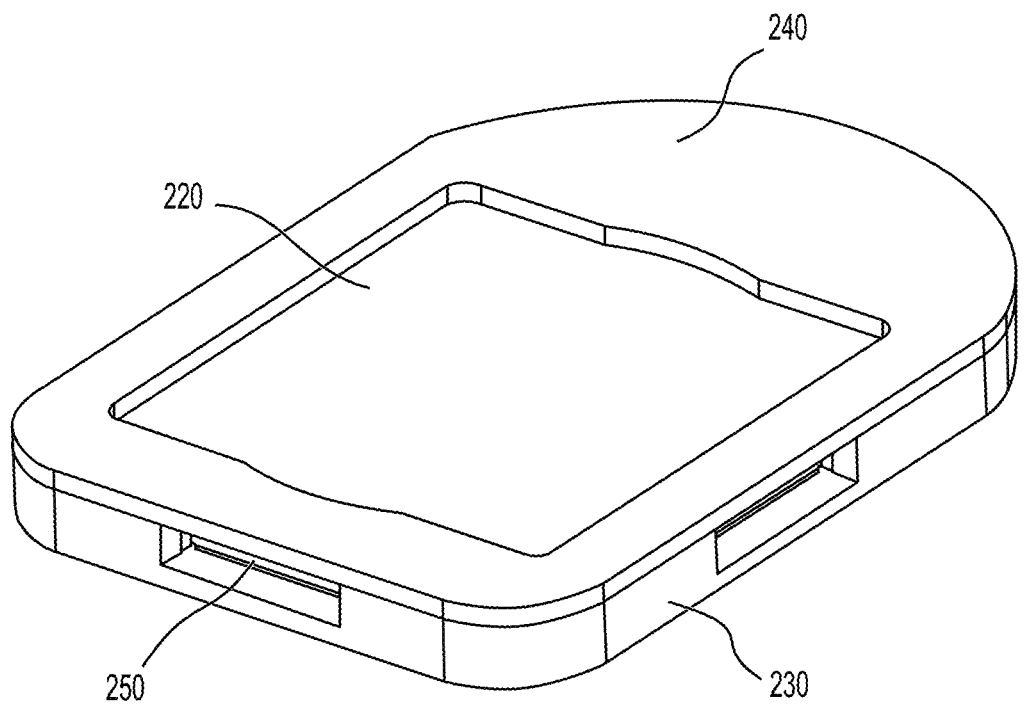
FIG. 9 is a perspective view of an opposing second side of the capsule of FIG. 8.

FIG. 8 is a perspective view of a first side of another capsule for an aerosol-generating device according to an example embodiment. FIG. 9 is a perspective view of an opposing second side of the capsule of FIG. 8. Referring to FIGS. 8-9, the capsule 200 may be configured to be received within an aerosol-generating device (e.g., heat-not-burn aerosol-generating device). In the drawings, the capsule 200 has a laminar structure and a generally planar form. The proximal end of the capsule 200 may have a curved proximal edge, and the opposing distal end may have a linear distal edge. In addition, a pair of linear side edges may connect the curved proximal edge and the linear distal edge. The pair of linear side edges may be parallel to each other. Furthermore, the junctions of the linear side edges with the linear distal edge may be in the form of rounded corners.

Although the capsule 200 is shown in the figures as resembling a rectangle with a semicircular end (e.g., elongated semicircle, semi-obround), it should be understood that other configurations may be employed. For instance, the shape may be circular such that the capsule 200 has a disk-like appearance. In another instance, the shape of the capsule 200 may be elliptical or racetrack-like. In other instances, the capsule 200 may have a polygonal shape (regular or irregular), including a triangle, a rectangle (e.g., square), a pentagon, a hexagon, a heptagon, or an octagon. The laminar structure and generally planar form of the capsule 200 may facilitate stacking so as to allow a plurality of capsules to be stored in an aerosol-generating device or other receptacle for dispensing a new capsule or receiving a depleted capsule.

The capsule 200 includes a first frame 230 and a second frame 240. The first frame 230 and the second frame 240 may be of the same shape and size (e.g., based on a plan view) and aligned such that the outer sidewalls are substantially flush with each other, although example embodiments are not limited thereto. The first frame 230 and the second frame 240 may be formed of a suitable polymer, such as polyether ether ketone (PEEK), liquid crystal polymer (LCP), and/or ultra-high molecular weight polyethylene (UHMWPE). The first frame 130 and the second frame 140 may be connected via a friction fit arrangement.

A first heater 210 is secured and exposed by the first frame 230. Similarly, a second heater 220 is secured and exposed by the second frame 240. As will be discussed in more detail herein, a third frame 250 is disposed between the first heater 210 and the second heater 220 (as well as between the first frame 230 and the second frame 240). The capsule 200 is configured to hold an aerosol-forming substrate, which may be within the third frame 250 and between the first heater 210 and the second heater 220. The first heater 210 and the second heater 220 are configured to heat the aerosol-forming substrate. As a result of the heating, the temperature of the aerosol-forming substrate may increase, and an aerosol may be generated. The first heater 210 and the second heater 220 may be in a form of a mesh, a perforated foil, or a combination thereof. For instance, both the first heater 210 and the second heater 220 may be in a form of a mesh. In another instance, both the first heater 210 and the second heater 220 may be in a form of a perforated foil (e.g., 80, 100, or 250 mesh equivalent). In yet another instance, one of the first heater 210 or the second heater 220 may be in a form of a mesh, while the other of the first heater 210 or the second heater 220 may be in a form of a perforated foil.

In an example embodiment, the first heater 210 and the second heater 220 are configured to undergo Joule heating (which is also known as ohmic/resistive heating) upon the application of an electric current thereto. Stated in more detail, the first heater 210 and the second heater 220 may be formed of conductors (same or different) and configured to produce heat when an electric current passes through the conductors. The electric current may be supplied from a power source (e.g., battery) within the aerosol-generating device. Suitable conductors for the first heater 210 and the second heater 220 include an iron-based alloy (e.g., stainless steel) and/or a nickel-based alloy (e.g., nichrome). The first heater 210 and the second heater 220 may have a thickness of about 0.0010 inch or less (e.g., 0.0005 inch) and a resistance of about 0.15-0.2 Ohm. Furthermore, although both the first heater 210 and the second heater 220 are shown in FIGS. 8-9, it should be understood that, in some example embodiments, only one of the first heater 210 or the second heater 220 is needed.

The electric current from the power source may be transmitted via electrodes configured to electrically contact the first heater 210 and the second heater 220 when the capsule 200 is inserted into the aerosol-generating device. In a non-limiting embodiment, the electrodes may be spring-loaded to enhance an engagement with the first heater 210 and the second heater 220 of the capsule 200. Also, the movement (e.g., engagement, release) of the electrodes may be achieved by mechanical actuation. The electrodes will be discussed in further detail herein. Furthermore, the supply of the electric current from the aerosol-generating device to the capsule 200 may be a manual operation (e.g., button-activated) or an automatic operation (e.g., puff-activated).

Figure 10:
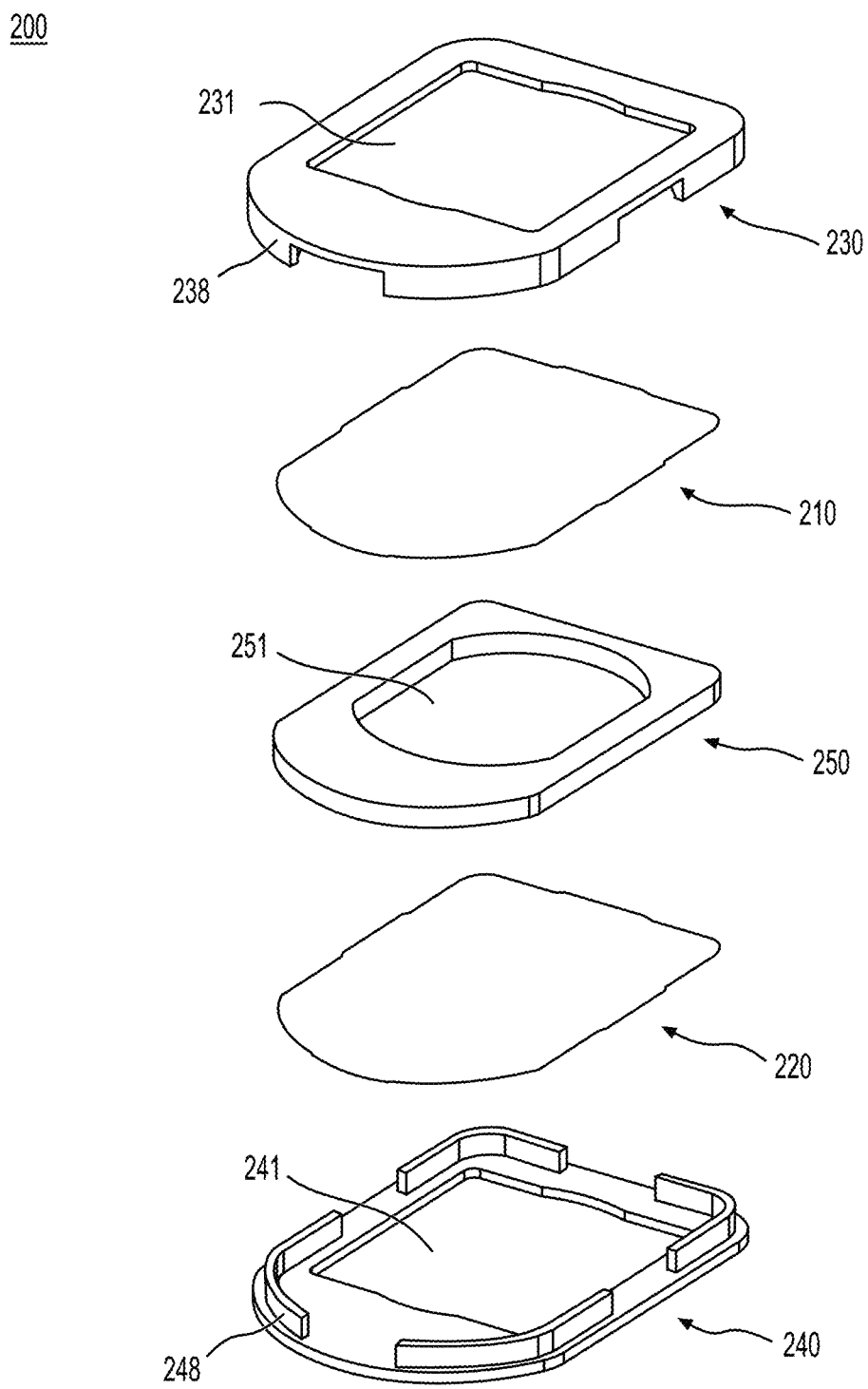
FIG. 10 is an exploded view of the capsule of FIG. 8.
Figure 11:
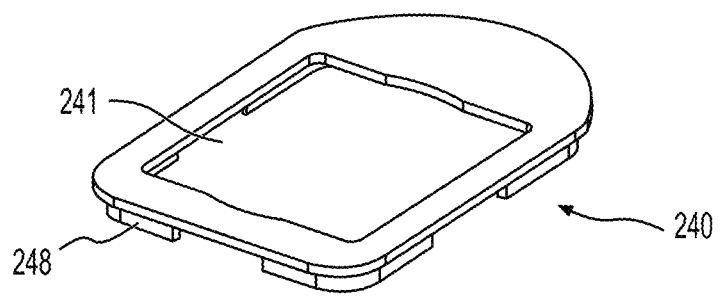
FIG. 11 is an exploded view of the capsule of FIG. 9.
Figure 11:
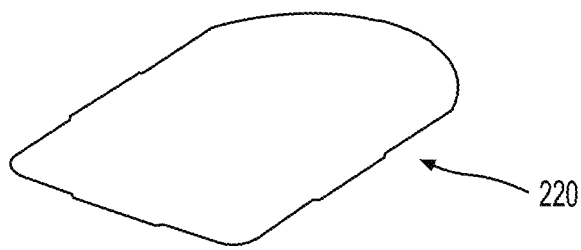
Figure 11:
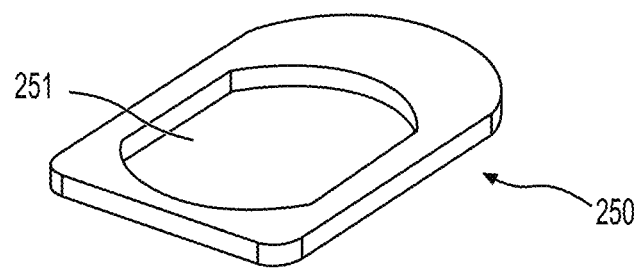
Figure 11:
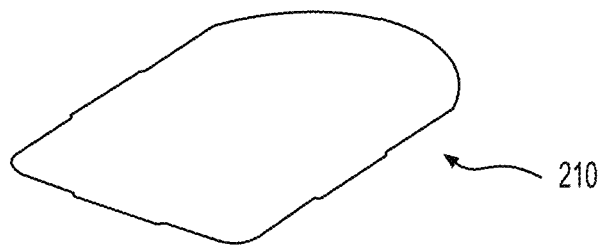
Figure 11:
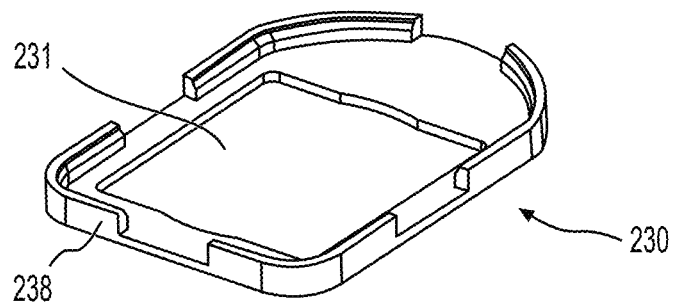

FIG. 10 is an exploded view of the capsule of FIG. 8. FIG. 11 is an exploded view of the capsule of FIG. 9. Referring to FIGS. 10-11, the first frame 230 has a first interior face and a first exterior face. In addition, the first frame 230 defines a first opening 231. In an example embodiment, the sidewall of the first opening 231 has opposing linear sections and, optionally, opposing curved sections, wherein one curved section may be adjacent to the proximal end of the first frame 230, and the other curved section may be adjacent to the opposing distal end of the first frame 230. The first heater 210 may be secured to the first interior face of the first frame 230 so as to be exposed by the first opening 231. From a different perspective, the first heater 210 may also be regarded as covering the first opening 231.

The second frame 240 has a second interior face and a second exterior face. In addition, the second frame 240 defines a second opening 241. In an example embodiment, the sidewall of the second opening 241 has opposing linear sections and, optionally, opposing curved sections, wherein one curved section may be adjacent to the proximal end of the second frame 240, and the other curved section may be adjacent to the opposing distal end of the second frame 240. The second heater 220 may be secured to the second interior face of the second frame 240 so as to be exposed by the second opening 241. From a different perspective, the second heater 220 may also be regarded as covering the second opening 241. The size and shape of the second opening 241 may correspond to (e.g., mirror) the size and shape of the first opening 231.

The third frame 250 defines a cavity 251 configured to receive an aerosol-forming substrate. In an example embodiment, the sidewall of the cavity 251 has opposing linear sections and opposing curved sections, wherein one curved section is adjacent to the proximal end of the third frame 250, and the other curved section is adjacent to the opposing distal end of the third frame 250. The third frame 250 may be substantially the same size as the first heater 210 and the second heater 220 based on a plan view (e.g., ±10% of a given dimension). In addition to the materials of construction for the first frame 230 and the second frame 240, the third frame 250 may also be formed of other suitable materials, such as ceramic, sintered glass, and/or consolidated fibers (e.g., cardboard).

The first heater 210 and the second heater 220 may be secured to the first frame 230 and the second frame 240, respectively, via a variety of attachment techniques. For instance, the attachment technique may involve injection molding (e.g., insert molding, over molding). In another instance, the attachment technique may involve ultrasonic welding. In other instances, the attachment technique may involve an adhesive (e.g., tape, glue) that has been deemed food-safe or otherwise acceptable by a regulatory authority. Alternatively, in lieu of a separate attachment technique, the first heater 210 and the second heater 220 may be clamped against the third frame 250 (or otherwise constrained) by the first frame 230 and the second frame 240, respectively.

The first frame 230 includes at least one first connector protruding from the first interior face of the first frame 230. The at least one first connector of the first frame 230 may be in a form of a first connector 238. In an example embodiment, the first connector 238 may extend along an edge of the first interior face of the first frame 230 in a form a ridge (e.g., first ridge). Although the first connector 238 is shown as being separated into a plurality of discrete structures (e.g., four discrete structures), it should be understood that example embodiments are not limited thereto. For instance, alternatively, the first connector 238 may be a single, continuous structure extending along the edge so as to completely surround the first interior face of the first frame 230.

Similarly, the second frame 240 includes at least one second connector protruding from the second interior face of the second frame 240. The at least one second connector of the second frame 240 may be in a form of a second connector 248. In an example embodiment, the second connector 248 may extend along a periphery of the second interior face of the second frame 240 in a form a ridge (e.g., second ridge) while offset or spaced apart from the edge. Although the second connector 248 is shown as being separated into a plurality of discrete structures (e.g., four discrete structures), it should be understood that example embodiments are not limited thereto. For instance, alternatively, the second connector 248 may be a single, continuous structure extending along the periphery so as to completely surround the second interior face of the second frame 240.

To assemble the capsule 200, the first frame 230 may be connected to the second frame 240 after an aerosol-forming substrate is disposed within the cavity 251 of the third frame 250. In such an instance, the third frame 250 will be sandwiched between the first heater 210 and the second heater 220 when the first frame 230 is connected to the second frame 240. During assembly, the at least one first connector of the first frame 230 is configured to engage with the at least one second connector of the second frame 240 to form at least one connection (e.g., four connections). In an example embodiment, the inner sidewall of the first connector 238 is configured to be in a friction fit arrangement with the outer sidewall of the second connector 248. Additionally, the inner sidewall of the first connector 238 may have an angled surface to facilitate the engagement with the outer sidewall of the second connector 248.

The height (e.g., degree of protrusion from the first interior face) of the first connector 238 may correspond to the height (e.g., degree of protrusion from the second interior face) of the second connector 248. In addition, a combined thickness of the first heater 210, the second heater 220, and the third frame 250 may correspond to the height of the second connector 248. As a result, the first connector 238 of the first frame 230 may contact the second interior face (e.g., offset surface) of the second frame 240 when the capsule 200 is assembled. Furthermore, the thickness of the first connector 238 of the first frame 230 may correspond to the offset distance of the second connector 248 from the edge of the second frame 240. As a result, the outer sidewall of the first frame 230 may be substantially flush with the outer sidewall of the second frame 240 when the capsule 200 is assembled.

Figure 12:
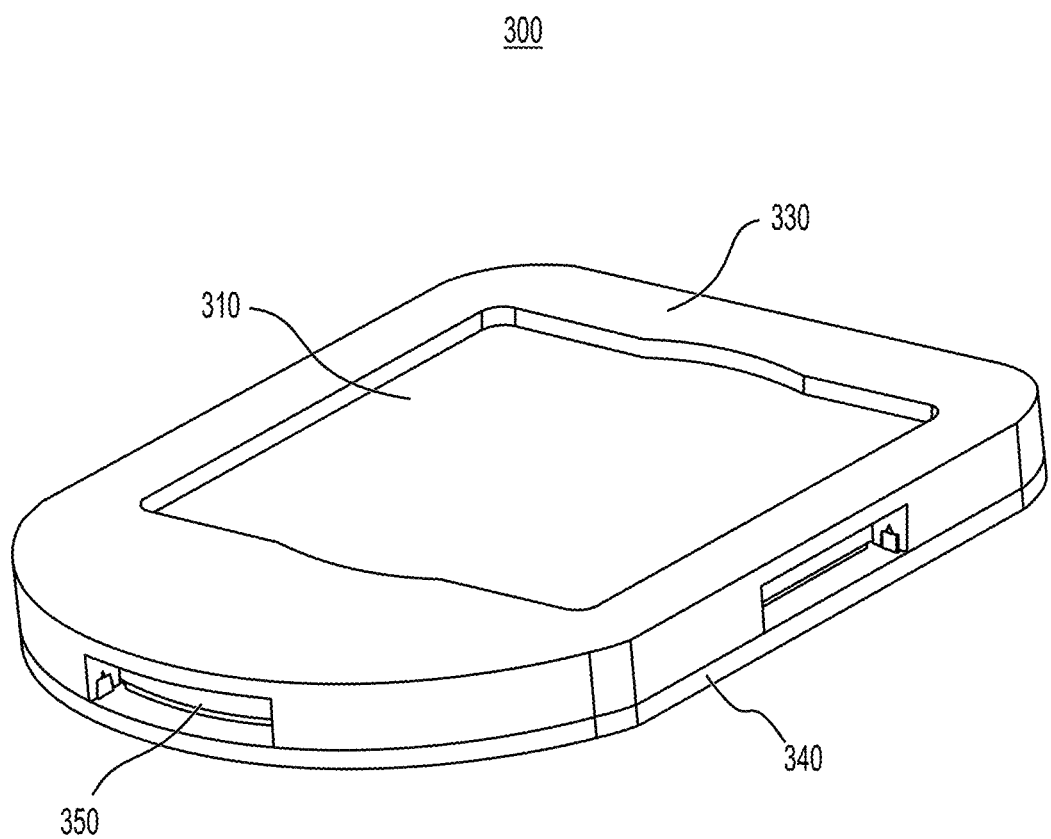
FIG. 12 is a perspective view of a first side of another capsule for an aerosol-generating device according to an example embodiment.
Figure 13:
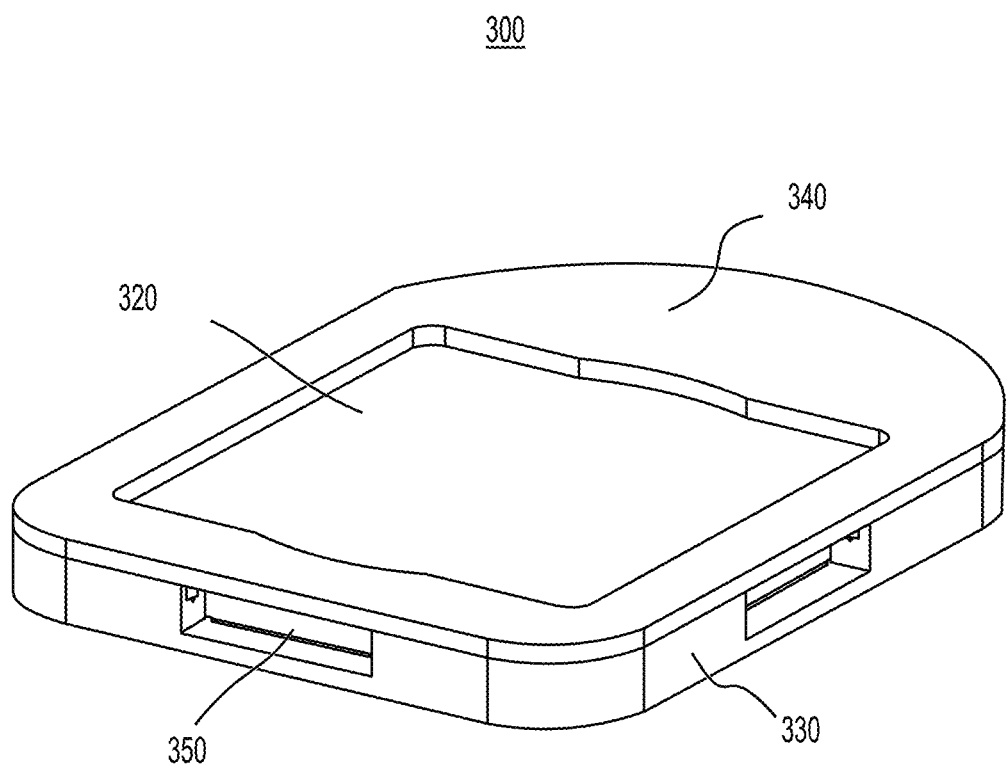
FIG. 13 is a perspective view of an opposing second side of the capsule of FIG. 12.

FIG. 12 is a perspective view of a first side of another capsule for an aerosol-generating device according to an example embodiment. FIG. 13 is a perspective view of an opposing second side of the capsule of FIG. 12. Referring to FIGS. 12-13, the capsule 300 may be configured to be received within an aerosol-generating device (e.g., heat-not-burn aerosol-generating device). The capsule 300 in FIGS. 12-13 may resemble the capsule 200 in FIGS. 8-9 while differing in the frame connection type, which will be discussed in more detail herein. In the drawings, the capsule 300 has a laminar structure and a generally planar form. The proximal end of the capsule 300 may have a curved proximal edge, and the opposing distal end may have a linear distal edge. In addition, a pair of linear side edges may connect the curved proximal edge and the linear distal edge. The pair of linear side edges may be parallel to each other. Furthermore, the junctions of the linear side edges with the linear distal edge may be in the form of rounded corners.

Although the capsule 300 is shown in the figures as resembling a rectangle with a semicircular end (e.g., elongated semicircle, semi-obround), it should be understood that other configurations may be employed. For instance, the shape may be circular such that the capsule 300 has a disk-like appearance. In another instance, the shape of the capsule 300 may be elliptical or racetrack-like. In other instances, the capsule 300 may have a polygonal shape (regular or irregular), including a triangle, a rectangle (e.g., square), a pentagon, a hexagon, a heptagon, or an octagon. The laminar structure and generally planar form of the capsule 300 may facilitate stacking so as to allow a plurality of capsules to be stored in an aerosol-generating device or other receptacle for dispensing a new capsule or receiving a depleted capsule.

The capsule 300 includes a first frame 330 and a second frame 340. The first frame 330 and the second frame 340 may be of the same shape and size (e.g., based on a plan view) and aligned such that the outer sidewalls are substantially flush with each other, although example embodiments are not limited thereto. The first frame 330 and the second frame 340 may be formed of a suitable polymer, such as polyether ether ketone (PEEK), liquid crystal polymer (LCP), and/or ultra-high molecular weight polyethylene (UHMWPE). The first frame 330 and the second frame 340 may be connected via a welded arrangement.

A first heater 310 is secured and exposed by the first frame 330. Similarly, a second heater 320 is secured and exposed by the second frame 340. As will be discussed in more detail herein, a third frame 350 is disposed between the first heater 310 and the second heater 320 (as well as between the first frame 330 and the second frame 340). The capsule 300 is configured to hold an aerosol-forming substrate, which may be within the third frame 350 and between the first heater 310 and the second heater 320. The first heater 310 and the second heater 320 are configured to heat the aerosol-forming substrate. As a result of the heating, the temperature of the aerosol-forming substrate may increase, and an aerosol may be generated. The first heater 310 and the second heater 320 may be in a form of a mesh, a perforated foil, or a combination thereof. For instance, both the first heater 310 and the second heater 320 may be in a form of a mesh. In another instance, both the first heater 310 and the second heater 320 may be in a form of a perforated foil (e.g., 80, 100, or 250 mesh equivalent). In yet another instance, one of the first heater 310 or the second heater 320 may be in a form of a mesh, while the other of the first heater 310 or the second heater 320 may be in a form of a perforated foil.

In an example embodiment, the first heater 310 and the second heater 320 are configured to undergo Joule heating (which is also known as ohmic/resistive heating) upon the application of an electric current thereto. Stated in more detail, the first heater 310 and the second heater 320 may be formed of conductors (same or different) and configured to produce heat when an electric current passes through the conductors. The electric current may be supplied from a power source (e.g., battery) within the aerosol-generating device. Suitable conductors for the first heater 310 and the second heater 320 include an iron-based alloy (e.g., stainless steel) and/or a nickel-based alloy (e.g., nichrome). The first heater 310 and the second heater 320 may have a thickness of about 0.0010 inch or less (e.g., 0.0005 inch) and a resistance of about 0.15-0.2 Ohm. Furthermore, although both the first heater 310 and the second heater 320 are shown in FIGS. 12-13, it should be understood that, in some example embodiments, only one of the first heater 310 or the second heater 320 is needed.

The electric current from the power source may be transmitted via electrodes configured to electrically contact the first heater 310 and the second heater 320 when the capsule 300 is inserted into the aerosol-generating device. In a non-limiting embodiment, the electrodes may be spring-loaded to enhance an engagement with the first heater 310 and the second heater 320 of the capsule 300. Also, the movement (e.g., engagement, release) of the electrodes may be achieved by mechanical actuation. The electrodes will be discussed in further detail herein. Furthermore, the supply of the electric current from the aerosol-generating device to the capsule 300 may be a manual operation (e.g., button-activated) or an automatic operation (e.g., puff-activated).

Figure 14:
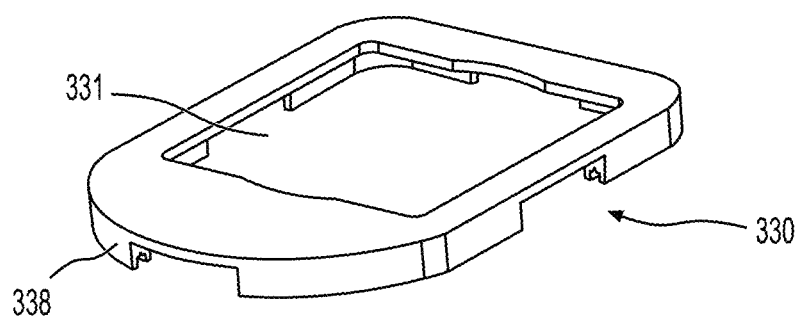
FIG. 14 is an exploded view of the capsule of FIG. 12.
Figure 14:
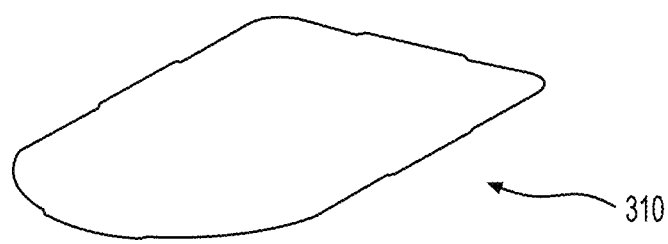
Figure 14:
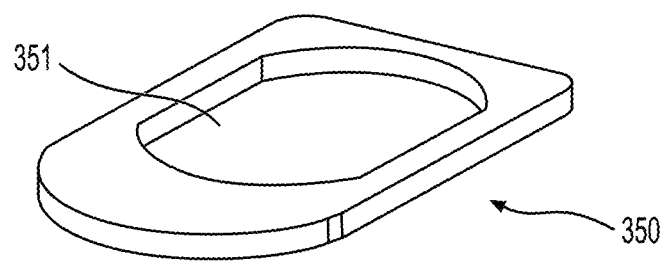
Figure 14:
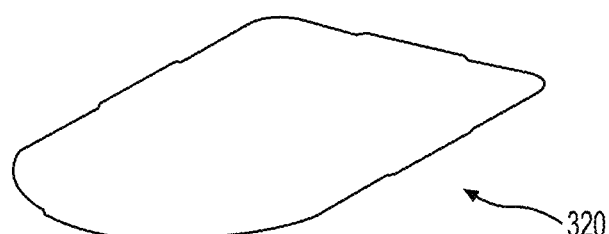
Figure 14:
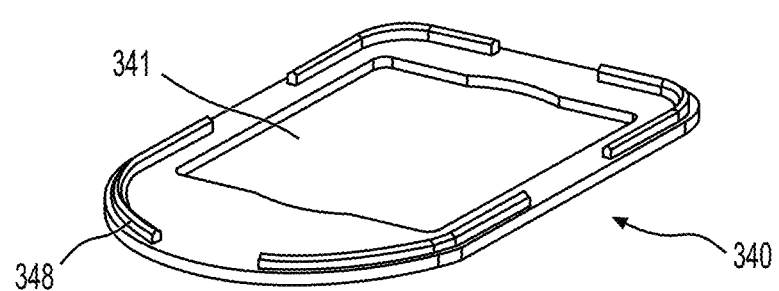
Figure 15:
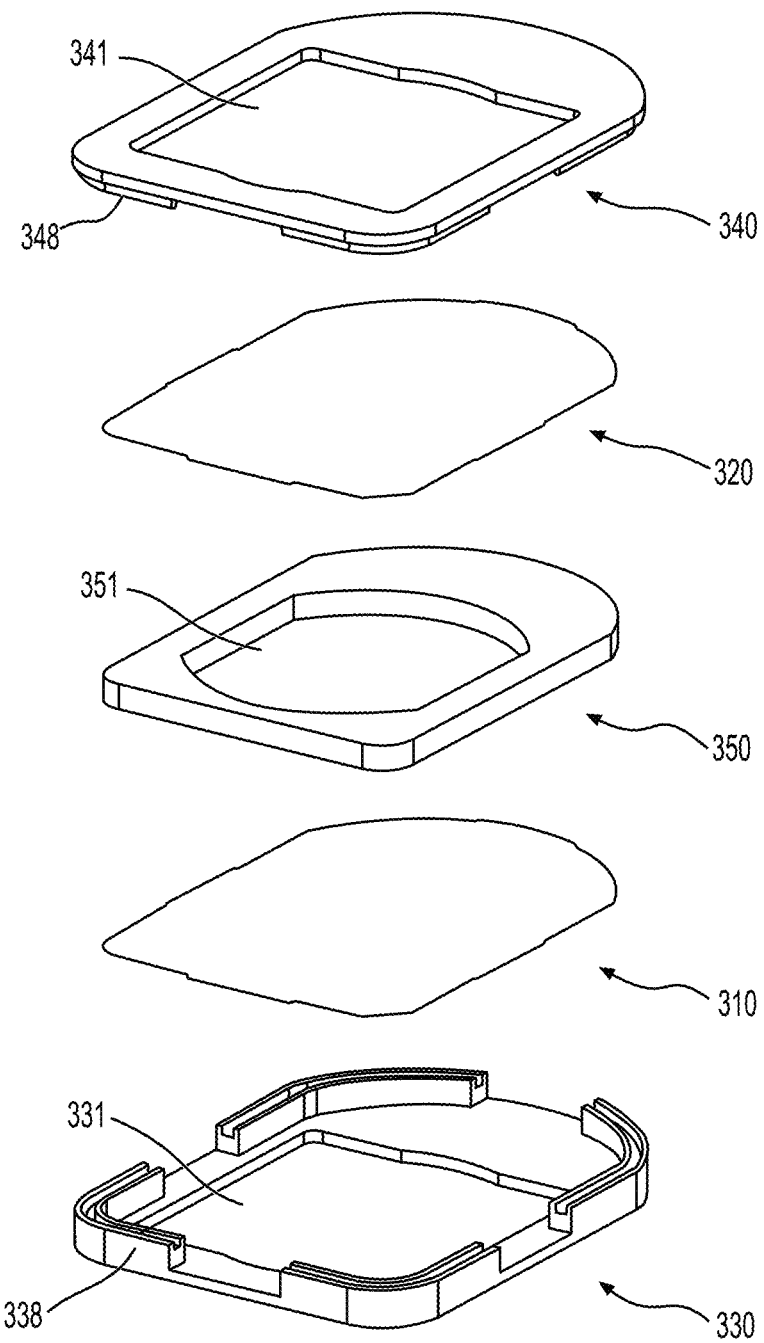
FIG. 15 is an exploded view of the capsule of FIG. 13.

FIG. 14 is an exploded view of the capsule of FIG. 12. FIG. 15 is an exploded view of the capsule of FIG. 13. Referring to FIGS. 14-15, the first frame 330 has a first interior face and a first exterior face. In addition, the first frame 330 defines a first opening 331. In an example embodiment, the sidewall of the first opening 331 has opposing linear sections and, optionally, opposing curved sections, wherein one curved section may be adjacent to the proximal end of the first frame 330, and the other curved section may be adjacent to the opposing distal end of the first frame 330. The first heater 310 may be secured to the first interior face of the first frame 330 so as to be exposed by the first opening 331. From a different perspective, the first heater 310 may also be regarded as covering the first opening 331.

The second frame 340 has a second interior face and a second exterior face. In addition, the second frame 340 defines a second opening 341. In an example embodiment, the sidewall of the second opening 341 has opposing linear sections and, optionally, opposing curved sections, wherein one curved section may be adjacent to the proximal end of the second frame 340, and the other curved section may be adjacent to the opposing distal end of the second frame 340. The second heater 320 may be secured to the second interior face of the second frame 340 so as to be exposed by the second opening 341. From a different perspective, the second heater 320 may also be regarded as covering the second opening 341. The size and shape of the second opening 341 may correspond to (e.g., mirror) the size and shape of the first opening 331.

The third frame 350 defines a cavity 351 configured to receive an aerosol-forming substrate. In an example embodiment, the sidewall of the cavity 351 has opposing linear sections and opposing curved sections, wherein one curved section is adjacent to the proximal end of the third frame 350, and the other curved section is adjacent to the opposing distal end of the third frame 350. The third frame 350 may be substantially the same size as the first heater 310 and the second heater 320 based on a plan view (e.g., ±10% of a given dimension).

The first heater 310 and the second heater 320 may be secured to the first frame 330 and the second frame 340, respectively, via a variety of attachment techniques. For instance, the attachment technique may involve injection molding (e.g., insert molding, over molding). In another instance, the attachment technique may involve ultrasonic welding. In other instances, the attachment technique may involve an adhesive (e.g., tape, glue) that has been deemed food-safe or otherwise acceptable by a regulatory authority. Alternatively, in lieu of a separate attachment technique, the first heater 310 and the second heater 320 may be clamped against the third frame 350 (or otherwise constrained) by the first frame 330 and the second frame 340, respectively.

The first frame 330 includes at least one first connector protruding from the first interior face of the first frame 330. The at least one first connector of the first frame 330 may be in a form of a first connector 338. In an example embodiment, the first connector 338 may extend along an edge of the first interior face of the first frame 330 in a form a ridge (e.g., first ridge). The ridge may define a trench extending along its entire length so as to resemble an elevated trench or a recessed/furrowed ridge. Although the first connector 338 is shown as being separated into a plurality of discrete structures (e.g., four discrete structures), it should be understood that example embodiments are not limited thereto. For instance, alternatively, the first connector 338 may be a single, continuous structure extending along the edge so as to completely surround the first interior face of the first frame 330.

Similarly, the second frame 340 includes at least one second connector protruding from the second interior face of the second frame 340. The at least one second connector of the second frame 340 may be in a form of a second connector 348. In an example embodiment, the second connector 348 may extend along a periphery of the second interior face of the second frame 340 in a form a ridge (e.g., second ridge) while offset or spaced apart from the edge. The ridge may have a tapered ridgeline and, as a result, may be referred to as a tapered ridge. Although the second connector 348 is shown as being separated into a plurality of discrete structures (e.g., four discrete structures), it should be understood that example embodiments are not limited thereto. For instance, alternatively, the second connector 348 may be a single, continuous structure extending along the periphery so as to completely surround the second interior face of the second frame 340.

To assemble the capsule 300, the first frame 330 may be connected to the second frame 340 after an aerosol-forming substrate is disposed within the cavity 351 of the third frame 350. In such an instance, the third frame 350 will be sandwiched between the first heater 310 and the second heater 320 when the first frame 330 is connected to the second frame 340. During assembly, the at least one first connector of the first frame 330 is configured to engage with the at least one second connector of the second frame 340 to form at least one connection (e.g., four connections). In an example embodiment, the recessed ridge of the first connector 338 is configured to mate with the tapered ridge of the second connector 348. In addition, the welded arrangement between the first connector 338 and the second connector 348 may be achieved via ultrasonic welding.

The depth of the trench in the first connector 338 may correspond to the height (e.g., degree of protrusion from the second interior face) of the second connector 348. In addition, a combined thickness of the first heater 310, the second heater 320, and the third frame 350 may correspond to the height (e.g., degree of protrusion from the first interior face) of the first connector 338. As a result, the first connector 338 of the first frame 330 may contact the second interior face (e.g., offset surface) of the second frame 340 when the capsule 300 is assembled. Furthermore, the outer sidewall of the first frame 330 may be substantially flush with the outer sidewall of the second frame 340 when the capsule 300 is assembled.

Figure 16:
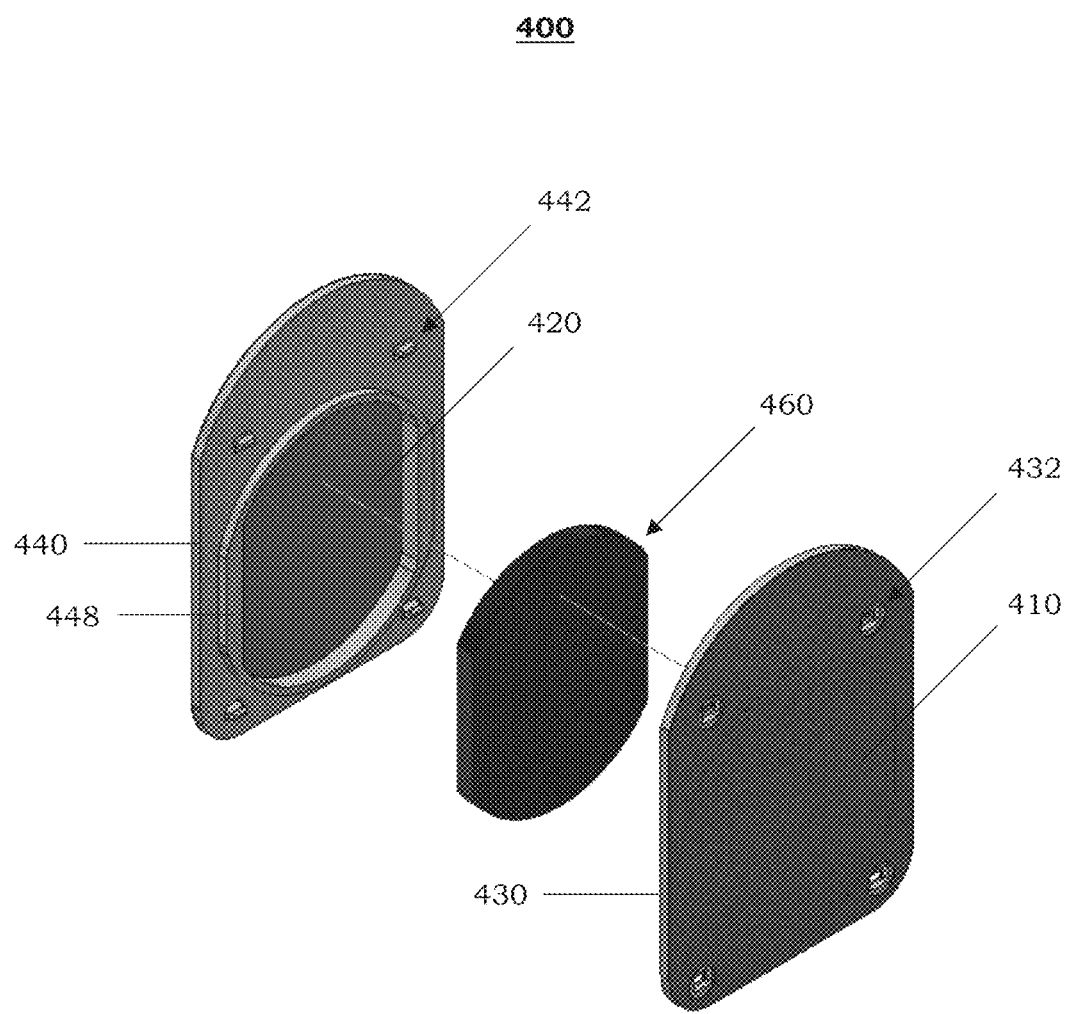
FIG. 16 is an exploded view of another capsule for an aerosol-generating device according to an example embodiment.

FIG. 16 is an exploded view of another capsule for an aerosol-generating device according to an example embodiment. The capsule 400 in FIG. 16 may resemble the capsule 100 in FIGS. 1-7 while differing in the details of the connectors, which will be discussed in more detail herein. As a result, the relevant disclosures above of the features in common should be understood to apply to this section and may not have been repeated in the interest of brevity.

Referring to FIG. 16, the capsule 400 includes a first frame 430 and a second frame 440. A first heater 410 is secured to the first frame 430, and a second heater 420 is secured to the second frame 440. The capsule 400 is configured to hold an aerosol-forming substrate 460, which may be between the first heater 410 and the second heater 420. The aerosol-forming substrate 460 may have a thickness ranging from 0.8-1.2 mm (e.g., 1.0 mm). With regard to composition, the aerosol-forming substrate may include about a 3:1-1.5:1 ratio (e.g., 2:1 ratio) with regard to tobacco and glycerin (e.g., 80 mg of tobacco and 35 mg of glycerin). Furthermore, the tobacco may be in a grounded form with a particle size ranging from 0.500 mm-0.750 mm, although example embodiments are not limited thereto. The first heater 410 and the second heater 420 are configured to heat the aerosol-forming substrate 460. Although both the first heater 410 and the second heater 420 are shown in FIG. 16, it should be understood that, in some example embodiments, only one of the first heater 410 or the second heater 420 is needed.

The first frame 430 has a first interior face and a first exterior face. In addition, the first frame 430 defines an opening (e.g., similar to the opening 131 in FIG. 3). The first heater 410 is secured to the first exterior face of the first frame 430 and covers the opening. Furthermore, the first heater 410 may define first apertures that are positioned and sized so as to expose the at least one first connector (e.g., first connector 432) when the first heater 410 is secured to the first frame 430.

The second frame 440 has a second interior face and a second exterior face. In addition, the second frame 440 defines an opening (e.g., second opening). The second frame 440 also includes a rim 448 around the opening so as to define a cavity configured to receive an aerosol-forming substrate 460. As shown in the figure, the inner sidewall of the rim 448 may be even with the inner sidewall of the opening in the second frame 440 so as to form a single inner sidewall. In an example embodiment, the inner sidewall of the cavity has opposing linear sections and opposing curved sections, wherein one curved section is adjacent to the proximal end of the second frame 440, and the other curved section is adjacent to opposing distal end of the second frame 440. The second heater 420 is secured to the second exterior face of the second frame 440 and covers the cavity. Furthermore, the second heater 420 may define second apertures that are positioned and sized so as to expose the at least one second connector (e.g., second connector 442), when the second heater 420 is secured to the second frame 440.

During assembly, the first frame 430 may be connected to the second frame 440 after an aerosol-forming substrate 460 is disposed within the cavity. In an example embodiment, the rim 448 of the second frame 440 will be seated within the opening of the first frame 430 as part of such a connection. For instance, the outer sidewall of the rim 448 may engage with the sidewall of the opening in the first frame 430. Such an engagement may be via an interference fit (which may also be referred to as a press fit or friction fit). Alternatively, there may be a clearance between the rim 448 and the opening so as to allow a relatively small degree of freedom between the second frame 440 and the first frame 430 (e.g., rotation of about ±10° or less).

The first frame 430 includes at least one first connector. The at least one first connector may be in a form of a first connector 432 disposed at four locations of the first frame 430. The second frame 440 includes at least one second connector protruding from the second interior face of the second frame 440. The at least one second connector may be in a form of a second connector 442 disposed at four locations of the second frame 440 (which correspond to the locations of the first connector 432 of the first frame 430). The at least one first connector of the first frame 430 is configured to engage with the at least one second connector of the second frame 440 to form at least one connection (e.g., four connections) such that the first interior face of the first frame 430 is adjacent to the second interior face of the second frame 440. In an example embodiment, the at least one first connector of the first frame 430 and the at least one second connector of the second frame 440 may be identical and reciprocally-oriented structures that complement each other so as to facilitate the formation of the at least one connection.

Each of the first connectors (e.g., first connector 432) may be in a form of a first catch portion situated adjacent to an orifice (e.g., first orifice) defined by the first frame 430, wherein the orifice has a recessed ledge or shelf disposed therein. In an example embodiment, the first connectors may be regarded as being integrally formed with the first frame 430. The first catch portion of each of the first connectors may protrude from the first interior face of the first frame 430. In particular, the first catch portion may include a first neck portion and a first nose portion, wherein the first neck portion protrudes from the first interior face of the first frame 430, and the first nose portion extends orthogonally relative to the first neck portion so as to form a first ledge that overlaps the first orifice defined by the first frame 430.

Each of the second connectors (e.g., second connector 442) may be in a form of a second catch portion situated adjacent to an orifice (e.g., second orifice) defined by the second frame 440, wherein the orifice has a recessed ledge or shelf disposed therein. In an example embodiment, the second connectors may be regarded as being integrally formed with the second frame 440. The second catch portion of each of the second connectors may protrude from the second interior face of the second frame 440. In particular, the second catch portion may include a second neck portion and a second nose portion, wherein the second neck portion protrudes from the second interior face of the second frame 440, and the second nose portion extends orthogonally relative to the second neck portion so as to form a second ledge that overlaps the second orifice defined by the second frame 440.

The at least one first connector of the first frame 430 is configured to be in an interlocking arrangement with the at least one second connector of the second frame 440 to form the connections (e.g., internal snap connections) for the capsule 400. For instance, to form a connection, a first catch portion of the first frame 430 is advanced into a corresponding second orifice of the second frame 440 such that the first neck portion deflects to allow the first nose portion to resiliently engage a corresponding recessed ledge within the second orifice of the second frame 440. As a result, a first ledge of a first connector will interlock or otherwise interface with a corresponding recessed ledge of a second connector. Similarly, when forming such a connection, a second catch portion of the second frame 440 is advanced into a corresponding first orifice of the first frame 430 such that the second neck portion deflects to allow the second nose portion to resiliently engage a corresponding recessed ledge within the first orifice of the first frame 430. As a result, a second ledge of a second connector will interlock or otherwise interface with a corresponding recessed ledge of a first connector.

However, in lieu of a mutual engagement of the connectors, it should be understood that, alternatively, a first connector 432 of the first frame 430 may be unilaterally engaged with a second connector 442 of the second frame 440. For instance, the catch portion may be omitted from the first connector 432 or the second connector 442 such that the connector only has the orifice and recessed ledge.

In a non-limiting embodiment, the height (e.g., degree of protrusion) of the first catch portion of the first connector 432 may be equal to or less than the thickness of the second frame 440 such that the first catch portion does not extend beyond the second exterior face of the second frame 440. Similarly, the height (e.g., degree of protrusion) of the second catch portion of the second connector 442 may be equal to or less than the thickness of the first frame 430 such that the second catch portion does not extend beyond the first exterior face of the first frame 430. Furthermore, when in an interlocking arrangement, the first neck portion of a first connector 432 may be parallel to the second neck portion of a second connector 442, although example embodiments are not limited thereto.

Figure 17:
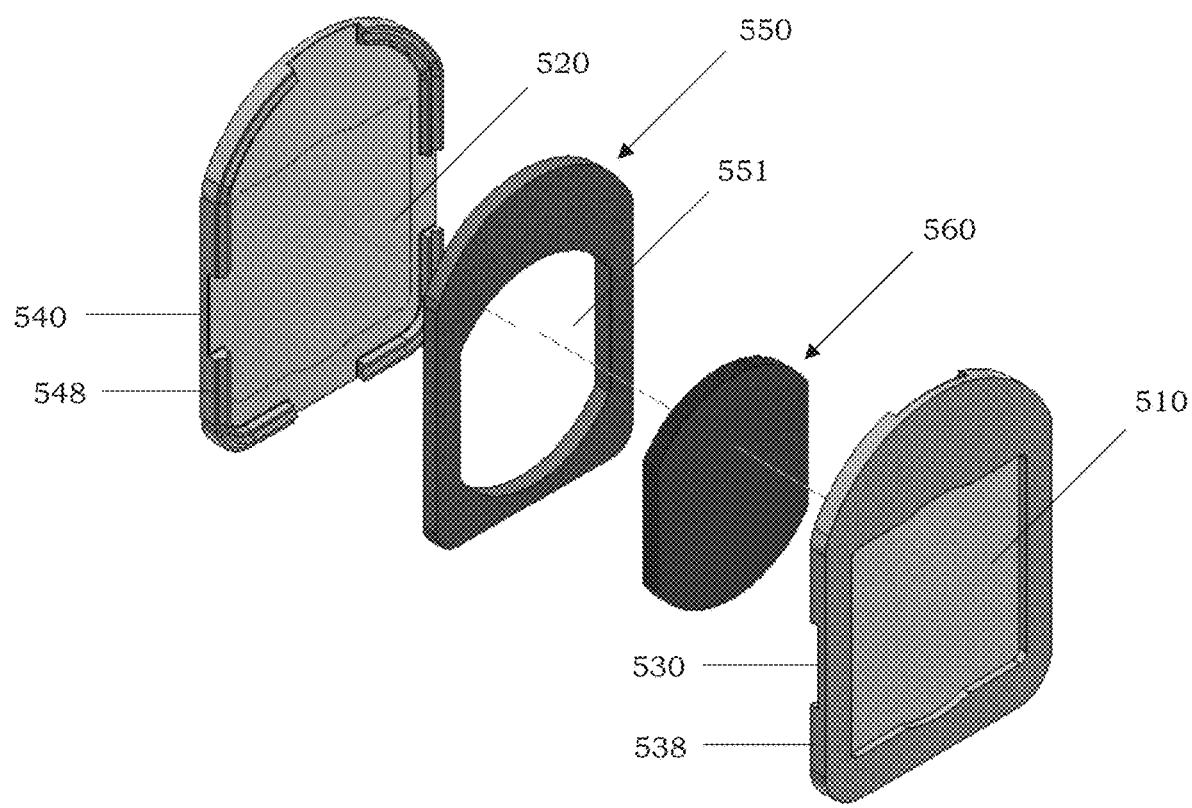
FIG. 17 is an exploded view of another capsule for an aerosol-generating device according to an example embodiment.

FIG. 17 is an exploded view of another capsule for an aerosol-generating device according to an example embodiment. The capsule 500 in FIG. 17 may resemble the capsule 300 in FIGS. 12-15 while differing in the details of the connectors, which will be discussed in more detail herein. As a result, the relevant disclosures above of the features in common should be understood to apply to this section and may not have been repeated in the interest of brevity.

Referring to FIG. 17, the capsule 500 includes a first frame 530 and a second frame 540. A first heater 510 is secured and exposed by the first frame 530. Similarly, a second heater 520 is secured and exposed by the second frame 540. A third frame 550 is disposed between the first heater 510 and the second heater 520 (as well as between the first frame 530 and the second frame 540). The capsule 500 is configured to hold an aerosol-forming substrate 560, which may be within the third frame 550 and between the first heater 510 and the second heater 520. The first heater 510 and the second heater 520 are configured to heat the aerosol-forming substrate 560. Although both the first heater 510 and the second heater 520 are shown in FIG. 17, it should be understood that, in some example embodiments, only one of the first heater 510 or the second heater 520 is needed.

The first frame 530 has a first interior face and a first exterior face. In addition, the first frame 530 defines a first opening (e.g., similar to the first opening 331 in FIG. 14). The first heater 510 may be secured to the first interior face of the first frame 530 so as to be exposed by the first opening. From a different perspective, the first heater 510 may also be regarded as covering the first opening.

The second frame 540 has a second interior face and a second exterior face. In addition, the second frame 540 defines a second opening (e.g., similar to the second opening 341 in FIG. 14). The second heater 520 may be secured to the second interior face of the second frame 540 so as to be exposed by the second opening. From a different perspective, the second heater 520 may also be regarded as covering the second opening. In an example embodiment, the size and shape of the second opening of the second frame 540 may correspond to (e.g., mirror) the size and shape of the first opening of the first frame 530.

The third frame 550 defines a cavity 551 configured to receive an aerosol-forming substrate 560. In an example embodiment, the sidewall of the cavity 551 has opposing linear sections and opposing curved sections, wherein one curved section is adjacent to the proximal end of the third frame 550, and the other curved section is adjacent to the opposing distal end of the third frame 550. The third frame 550 may be substantially the same size as the first heater 510 and the second heater 520 based on a plan view (e.g., ±10% of a given dimension).

The first frame 530 includes at least one first connector protruding from the first interior face of the first frame 530. The at least one first connector of the first frame 530 may be in a form of a first connector 538. In an example embodiment, the first connector 538 may extend along an edge of the first interior face of the first frame 530 in a form a ridge (e.g., first ridge). The ridge may define a trench extending along its entire length so as to resemble an elevated trench or a recessed/furrowed ridge. In addition or in the alternative, the ridge may have a tapered ridgeline and, as a result, may be referred to as a tapered ridge. Although the first connector 538 is shown as being separated into a plurality of discrete structures (e.g., four discrete structures), it should be understood that example embodiments are not limited thereto. For instance, alternatively, the first connector 538 may be a single, continuous structure extending along the edge so as to completely surround the first interior face of the first frame 530.

Similarly, the second frame 540 includes at least one second connector protruding from the second interior face of the second frame 540. The at least one second connector of the second frame 540 may be in a form of a second connector 548. The second connector 548 of the second frame 540 and the first connector 538 of the first frame 530 are complementary structures configured to mate with each other. In an example embodiment, the second connector 548 may extend along an edge of the second interior face of the second frame 540 in a form a ridge (e.g., second ridge). The ridge may define a trench extending along its entire length so as to resemble an elevated trench or a recessed/furrowed ridge. In addition or in the alternative, the ridge may have a tapered ridgeline and, as a result, may be referred to as a tapered ridge. Although the second connector 548 is shown as being separated into a plurality of discrete structures (e.g., four discrete structures), it should be understood that example embodiments are not limited thereto. For instance, alternatively, the second connector 548 may be a single, continuous structure extending along the periphery so as to completely surround the second interior face of the second frame 540.

In the non-limiting embodiment illustrated in FIG. 17 where the first connector 538 of the first frame 530 is separated into four discrete structures, two of the structures may be elevated trenches, while the other two structures may be tapered ridges. Conversely, the second connector 548 of the second frame 540 may be separated into four discrete structures, wherein two of the structures are tapered ridges, while the other two structures are elevated trenches. The mixed set of elevated trenches and tapered ridges of the first frame 530 are configured to mate with the mixed set of tapered ridges and elevated trenches, respectively, of the second frame 540 during the assembly of the capsule 500. It should be understood that various combinations of elevated trenches and the tapered ridges are possible for the first frame 530 and the second frame 540.

When the mixed set of elevated trenches and tapered ridges of each frame are grouped such that the elevated trenches are on one linear side edge while the tapered ridges are on the other linear side edge, as shown in FIG. 17, the first frame 530 and the second frame 540 may be identical parts. In such an instance, orienting the first frame 530 and the second frame 540 to face each other for mating will result in a complementary arrangement. As a result, one part may be used interchangeably as the first frame 530 or the second frame 540, thus simplifying the method of manufacturing.

Figure 18:
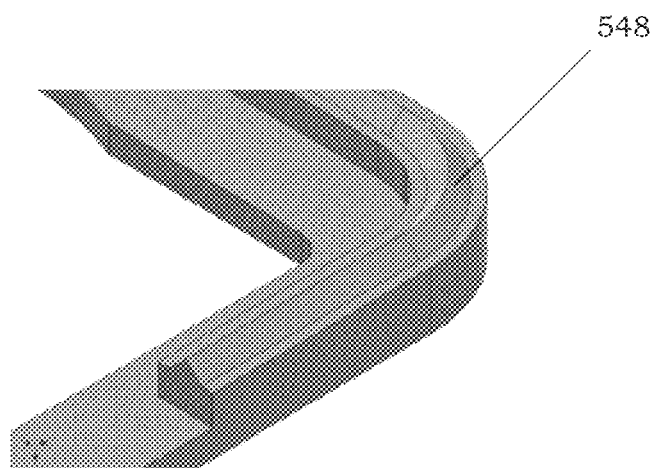
FIG. 18 is an enlarged view of a second connector of the second frame of FIG. 17.

FIG. 18 is an enlarged view of a second connector of the second frame of FIG. 17. Referring to FIG. 18, a second connector 548 of the second frame 540 may be in a form of a ridge having a shoulder portion and an inclined portion that rises from the shoulder portion to form a tapered ridgeline. The tapered ridgeline may function as an energy director during assembly (e.g., to facilitate welding). A corresponding first connector 538 of the first frame 530 may be in a form of a ridge resembling an elevated trench, wherein the ridge has a rim portion and a declining portion that slopes downward from the rim portion to form a V-shaped valley. In an example embodiment of a connection, the inclined portion of the second connector 548 is configured to be seated within the declining portion of the first connector 538, while the shoulder portion of the second connector 548 interfaces with the rim portion of the first connector 538. Thus, the engagement surfaces of the first connector 538 and the second connector 548 may be inversely configured to facilitate mating.

To assemble the capsule 500, the first frame 530 may be connected to the second frame 540 after an aerosol-forming substrate 560 is disposed within the cavity 551 of the third frame 550. In such an instance, the third frame 550 will be sandwiched between the first heater 510 and the second heater 520 when the first frame 530 is connected to the second frame 540. During assembly, the at least one first connector of the first frame 530 is configured to engage with the at least one second connector of the second frame 540 to form at least one connection (e.g., four connections). As discussed supra, an elevated trench (and/or tapered ridge) of the first connector 538 is configured to mate with a corresponding tapered ridge (and/or elevated trench) of the second connector 548. In addition, the joinder between the first connector 538 of the first frame 530 and the second connector 548 of the second frame 540 may be achieved via a welded arrangement (e.g., ultrasonic welding). Furthermore, the outer sidewall of the first frame 530 may be substantially flush with the outer sidewall of the second frame 540 when the capsule 500 is assembled, although example embodiments are not limited thereto.

Figure 19:
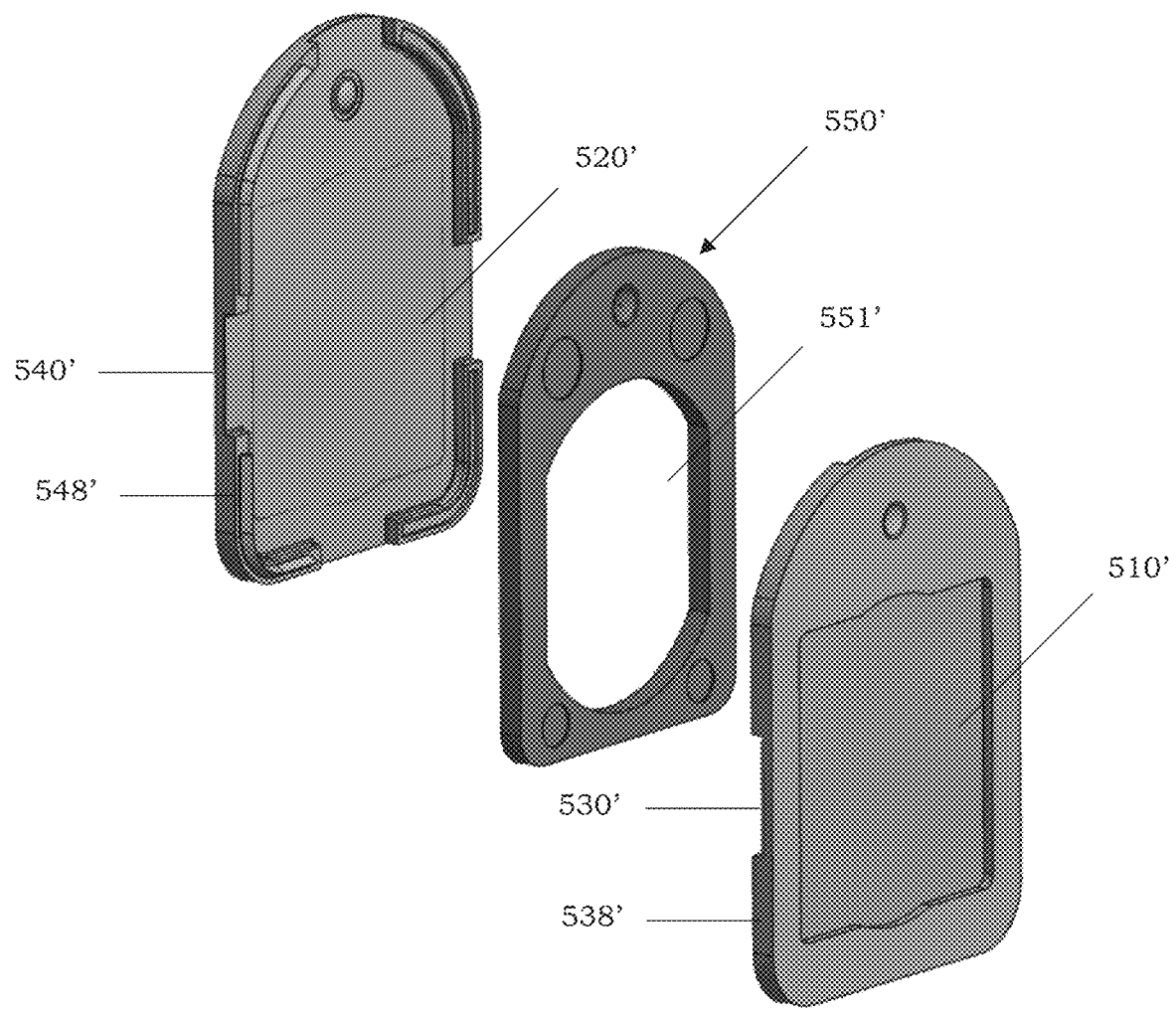
FIG. 19 is an exploded view of another capsule for an aerosol-generating device according to an example embodiment.

FIG. 19 is an exploded view of another capsule for an aerosol-generating device according to an example embodiment. The capsule 500' in FIG. 19 may resemble the capsule 500 in FIG. 17. In particular, the first heater 510', the second heater 520', the first frame 530', the first connector 538', the second frame 540', the second connector 548', the third frame 550', and the cavity 551' of FIG. 19 may be substantially as described with regard to the first heater 510, the second heater 520, the first frame 530, the first connector 538, the second frame 540, the second connector 548, the third frame 550, and the cavity 551 of FIG. 17. In addition, although not specifically illustrated in FIG. 19, an aerosol-forming substrate similar to the aerosol-forming substrate 560 in FIG. 17 will be disposed within the capsule 500' during assembly. As a result, the relevant disclosures above of the features in common should be understood to apply to this section and may not have been repeated in the interest of brevity. On the other hand, the differing aspects (e.g., connectors) which will be discussed in more detail herein.

In the non-limiting embodiment illustrated in FIG. 19 where the first connector 538' of the first frame 530' is separated into four discrete structures, two of the structures may be elevated trenches, while the other two structures may be tapered ridges. Conversely, the second connector 548' of the second frame 540' may be separated into four discrete structures, wherein two of the structures are tapered ridges, while the other two structures are elevated trenches. For the first frame 530' and the second frame 540', the elevated trenches may have a planar bottom (as opposed to a V-shaped bottom), although example embodiments are not limited thereto. The mixed set of elevated trenches and tapered ridges of the first frame 530' are configured to mate with the mixed set of tapered ridges and elevated trenches, respectively, of the second frame 540' during the assembly of the capsule 500'. It should be understood that various combinations of elevated trenches and the tapered ridges are possible for the first frame 530' and the second frame 540'.

When the mixed set of elevated trenches and tapered ridges of each frame are grouped such that the elevated trenches are on one linear side edge while the tapered ridges are on the other linear side edge, as shown in FIG. 19, the first frame 530' and the second frame 540' may be identical parts. In such an instance, orienting the first frame 530' and the second frame 540' to face each other for mating will result in a complementary arrangement. As a result, one part may be used interchangeably as the first frame 530' or the second frame 540', thus simplifying the method of manufacturing. Furthermore, the dimpled portions of the first frame 530', the second frame 540', and the third frame 550' may be from an injection molding process. In this regard, the size, location, and/or shape of the dimpled portions may differ (or the dimpled portions may be absent altogether) depending on the fabrication technique.

Figure 20:
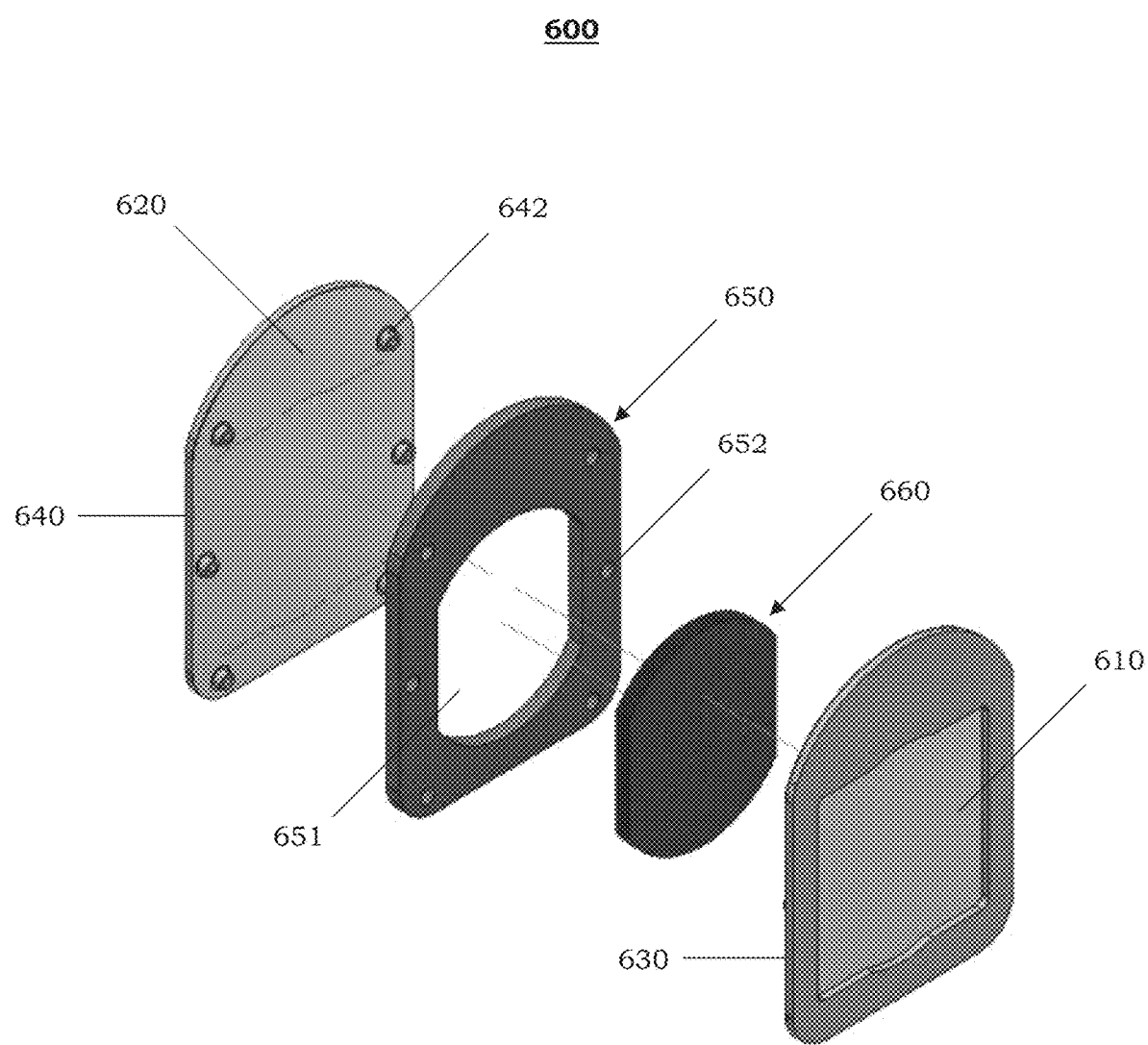
FIG. 20 is an exploded view of another capsule for an aerosol-generating device according to an example embodiment.

FIG. 20 is an exploded view of another capsule for an aerosol-generating device according to an example embodiment. The capsule 600 in FIG. 20 may resemble aspects of the capsule 300 in FIGS. 12-15 while differing in, for instance, the frame connection type, which will be discussed in more detail herein. As a result, the relevant disclosures above of the features in common should be understood to apply to this section and may not have been repeated in the interest of brevity.

Referring to FIG. 20, the capsule 600 includes a first frame 630 and a second frame 640. A first heater 610 is secured and exposed by the first frame 630. Similarly, a second heater 620 is secured and exposed by the second frame 640. A third frame 650 is disposed between the first heater 610 and the second heater 620 (as well as between the first frame 630 and the second frame 640). The capsule 600 is configured to hold an aerosol-forming substrate 660, which may be within the third frame 650 and between the first heater 610 and the second heater 620. The first heater 610 and the second heater 620 are configured to heat the aerosol-forming substrate 660. Although both the first heater 610 and the second heater 620 are shown in FIG. 20, it should be understood that, in some example embodiments, only one of the first heater 610 or the second heater 620 is needed.

The first frame 630 has a first interior face and a first exterior face. In addition, the first frame 630 defines a first opening (e.g., similar to the first opening 331 in FIG. 14). The first heater 610 may be secured to the first interior face of the first frame 630 so as to be exposed by the first opening. From a different perspective, the first heater 610 may also be regarded as covering the first opening.

The second frame 640 has a second interior face and a second exterior face. In addition, the second frame 640 defines a second opening (e.g., similar to the second opening 341 in FIG. 14). The second heater 620 may be secured to the second interior face of the second frame 640 so as to be exposed by the second opening. From a different perspective, the second heater 620 may also be regarded as covering the second opening. In an example embodiment, the size and shape of the second opening of the second frame 640 may correspond to (e.g., mirror) the size and shape of the first opening of the first frame 630.

The third frame 650 defines a cavity 651 configured to receive an aerosol-forming substrate 660. Additionally, the third frame 650 defines apertures 652 configured to receive connectors of the first frame 630 and the second frame 640 during the assembly of the capsule 600. Although six apertures 652 (e.g., six per side for blind holes or six total for through holes) are illustrated in connection with the third frame 650, it should be understood that other quantities (e.g., four) may be suitable. In an example embodiment, the sidewall of the cavity 651 has opposing linear sections and opposing curved sections, wherein one curved section is adjacent to the proximal end of the third frame 650, and the other curved section is adjacent to the opposing distal end of the third frame 650. The third frame 650 may be substantially the same size as the first heater 610 and the second heater 620 based on a plan view (e.g., ±10% of a given dimension).

The first frame 630 includes at least one connector (e.g., first connector) protruding from the first interior face of the first frame 630. For instance, the at least one connector of the first frame 630 may be in a form of a projection on the first interior face. The at least one connector of the first frame 630 may resemble the connector 642 of the second frame 640, which will be discussed in more detail herein. In an example embodiment, the connectors of the first frame 630 may be arranged along a periphery of the first interior face so as to be aligned with the apertures 652 in the third frame 650 during assembly.

Similarly, the second frame 640 includes at least one connector (e.g., second connector) protruding from the second interior face of the second frame 640. The at least one connector of the second frame 640 may be in a form of a plurality of connectors 642. Although six connectors 642 are illustrated in connection with the second frame 640, it should be understood that other quantities (e.g., four) may be suitable. In an example embodiment, the connectors 642 may be arranged along a periphery of the second interior face of the second frame 640 so as to be aligned with corresponding apertures 652 in the third frame 650 during assembly. It should be understood that the pattern of the connectors and corresponding apertures 652 may be varied such that each of the apertures 652 in the third frame 650 receives connectors of both the first frame 630 and the second frame 640, each of the apertures 652 in the third frame 650 receives only one connector of the first frame 630 or the second frame 640, or a combination thereof.

In an example embodiment, the first frame 630 and the second frame 640 may be identical parts. As a result, one part may be used interchangeably as the first frame 630 or the second frame 640, thus simplifying the method of manufacturing.

Figure 21:
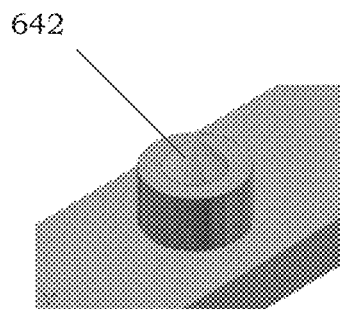
FIG. 21 is an enlarged view of a connector of the second frame of FIG. 20.

FIG. 21 is an enlarged view of a connector of the second frame of FIG. 20. Referring to FIG. 21, a connector 642 of the second frame 640 may be in a form of a projection having a cylindrical body and a conical tip. The conical tip may function as an energy director during assembly (e.g., to facilitate welding). In an example embodiment, the base of the conical tip may be smaller than the diameter of the cylindrical body such that the connector 642 has a shoulder portion. Although not shown, it should be understood that the base of the conical tip may, in the alternative, be the same size as than the diameter of the cylindrical body such that the connector 642 does not have a shoulder portion. Additionally, the second heater 620 may be provided with an opening for each connector 642 of the second frame 640 so that the connectors 642 can protrude therethrough when the second heater 620 is secured to the second interior face of the second frame 640. Similarly, the first heater 610 may be provided with an opening for each connector of the first frame 630 so that the connectors can protrude therethrough when the first heater 610 is secured to the first interior face of the first frame 630.

To assemble the capsule 600, the first frame 630 may be connected to the second frame 640 after an aerosol-forming substrate 660 is disposed within the cavity 651 of the third frame 650. In such an instance, the third frame 650 will be sandwiched between the first heater 610 and the second heater 620 when the first frame 630 is connected to the second frame 640. During assembly, a connector of the first frame 630 is configured to engage with a corresponding aperture 652 of the third frame 650 to form a connection. Similarly, a connector 642 of the second frame 640 is configured to engage with a corresponding aperture 652 of the third frame 650 to form a connection. In addition, the joinder between the frames via the connectors may be achieved via a welded arrangement (e.g., ultrasonic welding) or an interference fit. Furthermore, the outer sidewalls of the first frame 630, the second frame 640, and the third frame 650 may be substantially flush with each other when the capsule 600 is assembled, although example embodiments are not limited thereto.

Figure 22:
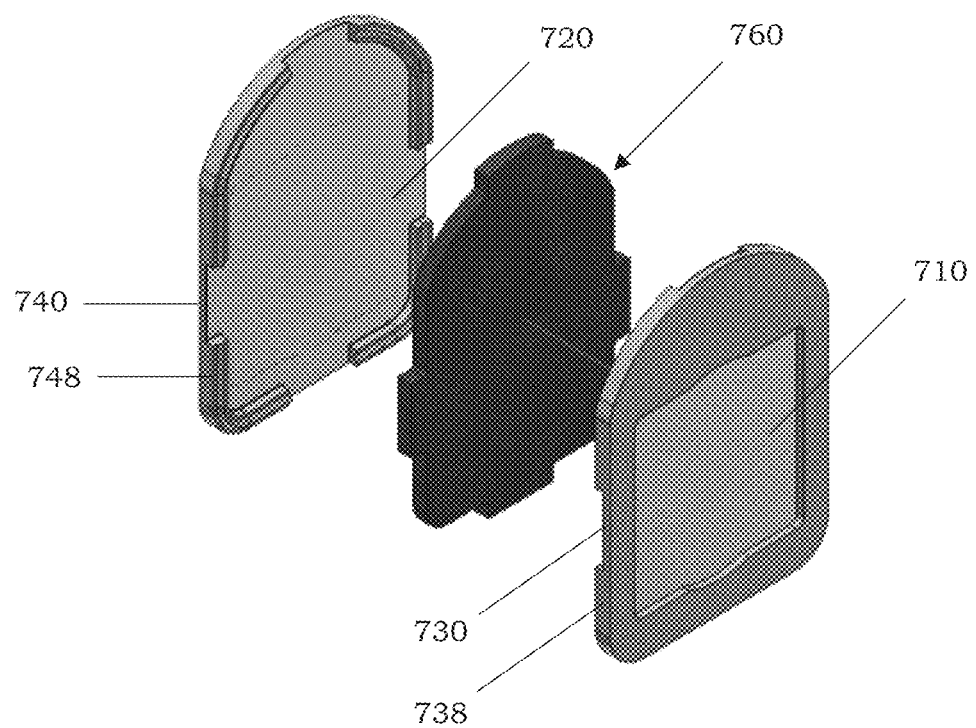
FIG. 22 is an exploded view of another capsule for an aerosol-generating device according to an example embodiment.

FIG. 22 is an exploded view of another capsule for an aerosol-generating device according to an example embodiment. The capsule 700 in FIG. 22 may resemble the capsule 500 in FIG. 17 while differing with regard to how the aerosol-forming substrate is disposed therein, which will be discussed in more detail herein. As a result, the relevant disclosures above of the features in common should be understood to apply to this section and may not have been repeated in the interest of brevity.

Referring to FIG. 22, the capsule 700 includes a first frame 730 and a second frame 740. A first heater 710 is secured and exposed by the first frame 730. Similarly, a second heater 720 is secured and exposed by the second frame 740. The capsule 700 is configured to hold an aerosol-forming substrate 760 between the first heater 710 and the second heater 720. The first heater 710 and the second heater 720 are configured to heat the aerosol-forming substrate 760. Although both the first heater 710 and the second heater 720 are shown in FIG. 22, it should be understood that, in some example embodiments, only one of the first heater 710 or the second heater 720 is needed.

The first frame 730 has a first interior face and a first exterior face. In addition, the first frame 730 defines a first opening (e.g., similar to the first opening 331 in FIG. 14). The first heater 710 may be secured to the first interior face of the first frame 730 so as to be exposed by the first opening. From a different perspective, the first heater 710 may also be regarded as covering the first opening.

The second frame 740 has a second interior face and a second exterior face. In addition, the second frame 740 defines a second opening (e.g., similar to the second opening 341 in FIG. 14). The second heater 720 may be secured to the second interior face of the second frame 740 so as to be exposed by the second opening. From a different perspective, the second heater 720 may also be regarded as covering the second opening. In an example embodiment, the size and shape of the second opening of the second frame 740 may correspond to (e.g., mirror) the size and shape of the first opening of the first frame 730.

The first frame 730 includes at least one first connector protruding from the first interior face of the first frame 730. The at least one first connector of the first frame 730 may be in a form of a first connector 738. In an example embodiment, the first connector 738 may extend along an edge of the first interior face of the first frame 730 in a form a ridge (e.g., first ridge). The ridge may define a trench extending along its entire length so as to resemble an elevated trench or a recessed/furrowed ridge. In addition or in the alternative, the ridge may have a tapered ridgeline and, as a result, may be referred to as a tapered ridge. Although the first connector 738 is shown as being separated into a plurality of discrete structures (e.g., four discrete structures), it should be understood that example embodiments are not limited thereto. For instance, alternatively, the first connector 738 may be a single, continuous structure extending along the edge so as to completely surround the first interior face of the first frame 730.

Similarly, the second frame 740 includes at least one second connector protruding from the second interior face of the second frame 740. The at least one second connector of the second frame 740 may be in a form of a second connector 748. The second connector 748 of the second frame 740 and the first connector 738 of the first frame 730 are complementary structures configured to mate with each other. In an example embodiment, the second connector 748 may extend along an edge of the second interior face of the second frame 740 in a form a ridge (e.g., second ridge). The ridge may define a trench extending along its entire length so as to resemble an elevated trench or a recessed/furrowed ridge. In addition or in the alternative, the ridge may have a tapered ridgeline and, as a result, may be referred to as a tapered ridge. Although the second connector 748 is shown as being separated into a plurality of discrete structures (e.g., four discrete structures), it should be understood that example embodiments are not limited thereto. For instance, alternatively, the second connector 748 may be a single, continuous structure extending along the periphery so as to completely surround the second interior face of the second frame 740.

In the non-limiting embodiment illustrated in FIG. 22 where the first connector 738 of the first frame 730 is separated into four discrete structures, two of the structures may be elevated trenches, while the other two structures may be tapered ridges. Conversely, the second connector 748 of the second frame 740 may be separated into four discrete structures, wherein two of the structures are tapered ridges, while the other two structures are elevated trenches. The mixed set of elevated trenches and tapered ridges of the first frame 730 are configured to mate with the mixed set of tapered ridges and elevated trenches, respectively, of the second frame 740 during the assembly of the capsule 700. It should be understood that various combinations of elevated trenches and the tapered ridges are possible for the first frame 730 and the second frame 740.

In an example embodiment, the first frame 730 and the second frame 740 may be identical parts. In such an instance, orienting the first frame 730 and the second frame 740 to face each other for mating will result in a complementary arrangement. As a result, one part may be used interchangeably as the first frame 730 or the second frame 740, thus simplifying the method of manufacturing.

To assemble the capsule 700, the first frame 730 may be connected to the second frame 740 after an aerosol-forming substrate 760 is disposed therebetween. In an example embodiment, the aerosol-forming substrate 760 may be sized and shaped so as to substantially fill the unoccupied space within the capsule 700. For instance, the aerosol-forming substrate 760 may have portions (e.g., laterally-extending portions) that are adjacent to the edges of the capsule 700 and within the gaps between adjacent connectors of the first frame 730 and the second frame 740. In addition, the first heater 710 and/or the second heater 720 may have a size and shape that corresponds to the aerosol-forming substrate 760. During assembly, the at least one first connector of the first frame 730 is configured to engage with the at least one second connector of the second frame 740 to form at least one connection (e.g., four connections). As discussed supra, an elevated trench (and/or tapered ridge) of the first connector 738 is configured to mate with a corresponding tapered ridge (and/or elevated trench) of the second connector 748. In addition, the joinder between the first connector 738 of the first frame 730 and the second connector 748 of the second frame 740 may be achieved via a welded arrangement (e.g., ultrasonic welding). Furthermore, the outer sidewall of the first frame 730 may be substantially flush with the outer sidewall of the second frame 740 when the capsule 700 is assembled, although example embodiments are not limited thereto.

Figure 23:
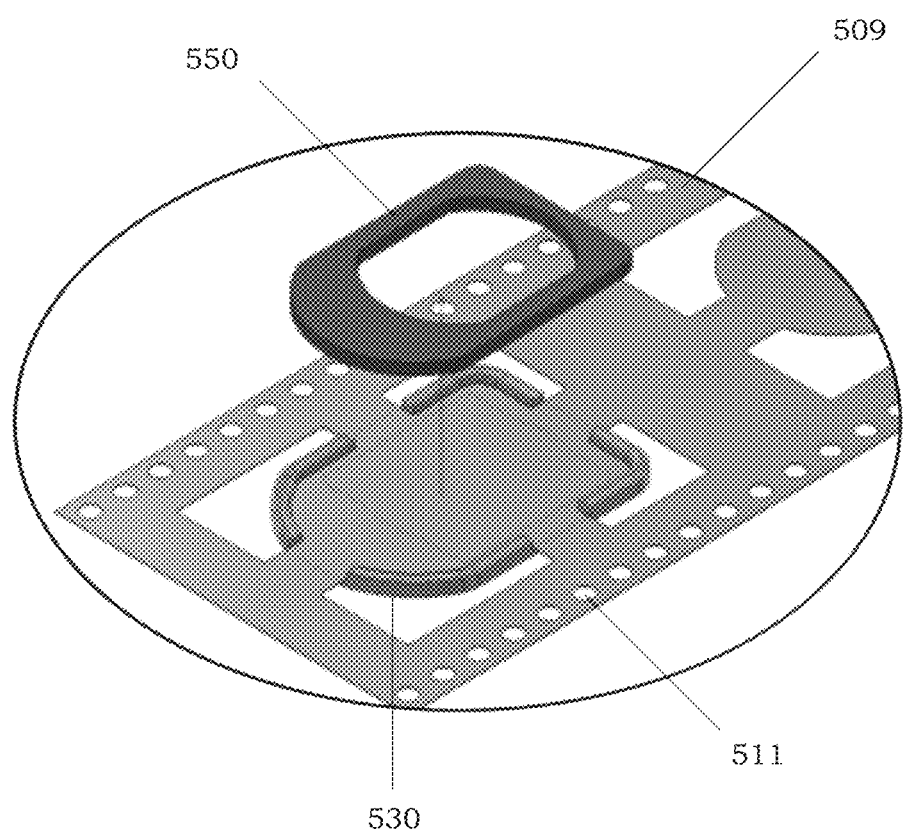
FIGS. 23-26 are perspective views of a method of manufacturing a capsule for an aerosol-generating device according to an example embodiment.

FIGS. 23-26 are perspective views of a method of manufacturing a capsule for an aerosol-generating device according to an example embodiment. Referring to FIG. 23, a first sheet 509 (e.g., first web) may be used to produce one or more first heaters (e.g., first heater 510). The first sheet 509 may be in a form of a mesh or a foil (e.g., that is pre- or post-perforated) and constructed of a material, as discussed supra, that is suitable for Joule heating. As shown, the first sheet 509 may be cut (e.g., die cut) to produce one or more heater patterns. Each heater pattern may include a primary portion and laterally-extending portions that link the primary portion to peripheral portions of the first sheet 509. Although the primary portion of the heater pattern is shown as being linked to the peripheral portions of the first sheet 509 by four laterally-extending portions, it should be understood that example embodiments are not limited thereto. For instance, two laterally-extending portions may be adequate to link the proximal end and the distal end of the primary portion of the heater pattern to the peripheral portions of the first sheet 509. In another instance, two laterally-extending portions may be adequate to link the sides of the primary portion of the heater pattern to the peripheral portions of the first sheet 509.

Additionally, the first sheet 509 may be provided with a plurality of holes 511 to facilitate the positioning and movement of the first sheet 509 during the method of manufacturing. For instance, a first series of the holes 511 may be provided along one edge of the first sheet 509, while a second series of the holes 511 may be provided along the opposite edge of the first sheet 509. As illustrated, the first series and the second series of the holes 511 may be arranged in parallel along a longitudinal direction of the first sheet 509. As a result, the first sheet 509 may be drawn from a first sheet source (e.g., a reel of the first sheet 509) by one or more drums with circumferentially-arranged protuberances configured to engage with the holes 511 and, thus, advance the first sheet 509 along the conveyance path when the one or more drums are rotated.

The first frame 530 may be separately fabricated and then attached to the primary portion of the heater pattern (e.g., via ultrasonic welding). In another instance, the first frame 530 may be simultaneously fabricated and attached to the primary portion of the heater pattern. This fabrication and attachment technique may involve injection molding (e.g., insert molding, over molding). In an example embodiment where only two laterally-extending portions are provided to link the primary portion of the heater pattern (e.g., the proximal end and the distal end of the primary portion) to the peripheral portions of the first sheet 509, the first connector (e.g., first connector 538) of the first frame 530 may be in the form of two discrete structures. After the fabrication of the first frame 530 and its attachment to the first sheet 509, the third frame 550 is seated between the first connectors of the first frame 530.

Figure 24:
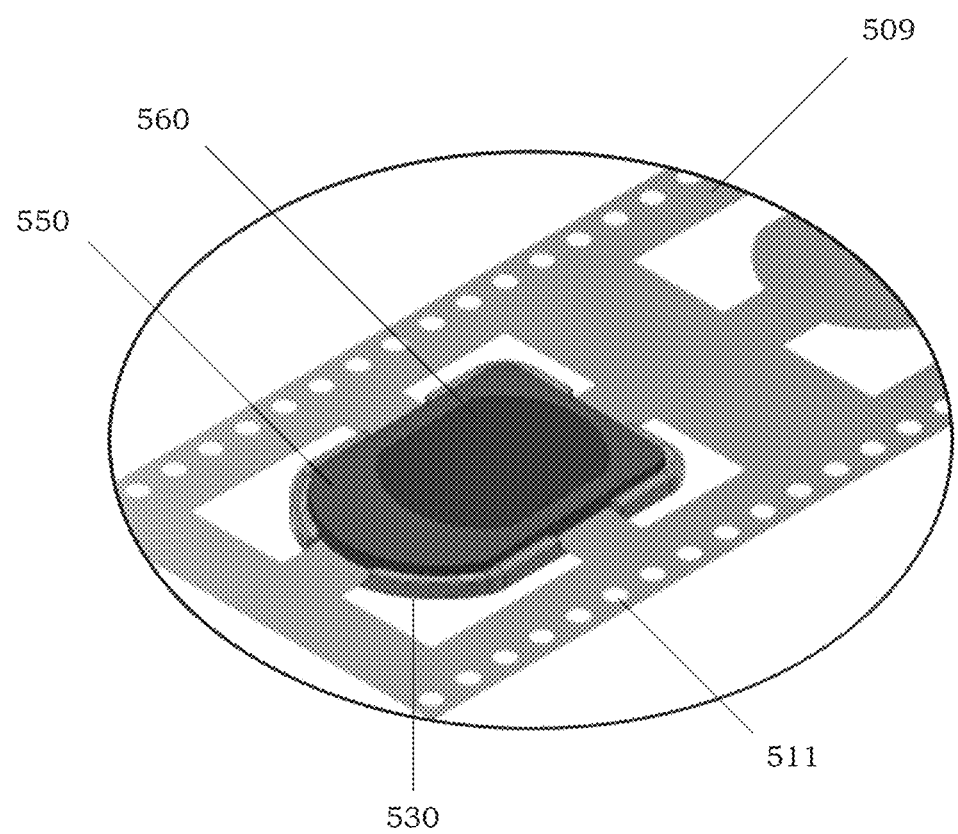

Referring to FIG. 24, an aerosol-forming substrate 560 is disposed within the cavity (e.g., cavity 551) of the third frame 550. The aerosol-forming substrate 560 may be in a consolidated form (e.g., sheet, tablet) that is configured to maintain its shape so as to allow the aerosol-forming substrate 560 to be placed in a unified manner within the cavity of the third frame 550. Alternatively, the aerosol-forming substrate 560 may be in a loose form (e.g., particles, fibers, grounds, fragments, shreds) that does not have a set shape but rather is configured to take on the shape of the cavity of the third frame 550 when introduced.

Figure 25:
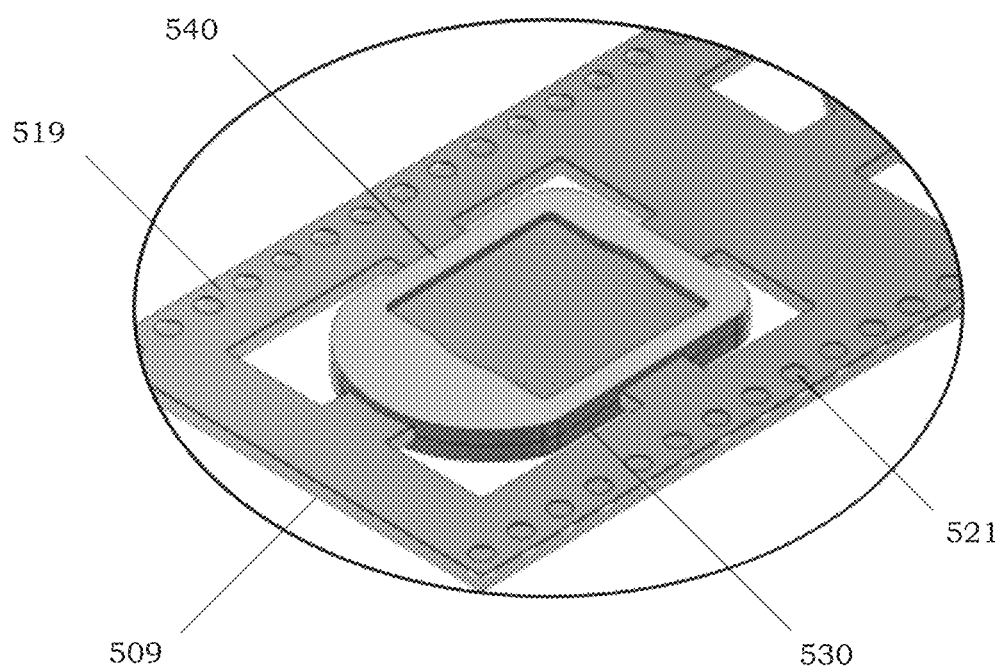

Referring to FIG. 25, a second sheet 519 (e.g., second web) may be used to produce one or more second heaters (e.g., second heater 520). The second sheet 519 may be as described in connection with the first sheet 509 and prepared in a similar manner to produce one or more heater patterns. In addition, the second frame 540 may be fabricated and attached to the heater pattern of the second sheet 519 in a similar manner as the fabrication and attachment of the first frame 530 to the heater pattern of the first sheet 509. In an example embodiment, the second sheet 519, the holes 521, and the second frame 540 are identical to the first sheet 509, the holes 511, and the first frame 530, respectively. The third frame 550 and the aerosol-forming substrate 560 may then be enclosed by connecting the second frame 540 to the first frame 530 via a welded arrangement, which may be achieved via ultrasonic welding.

Figure 26:
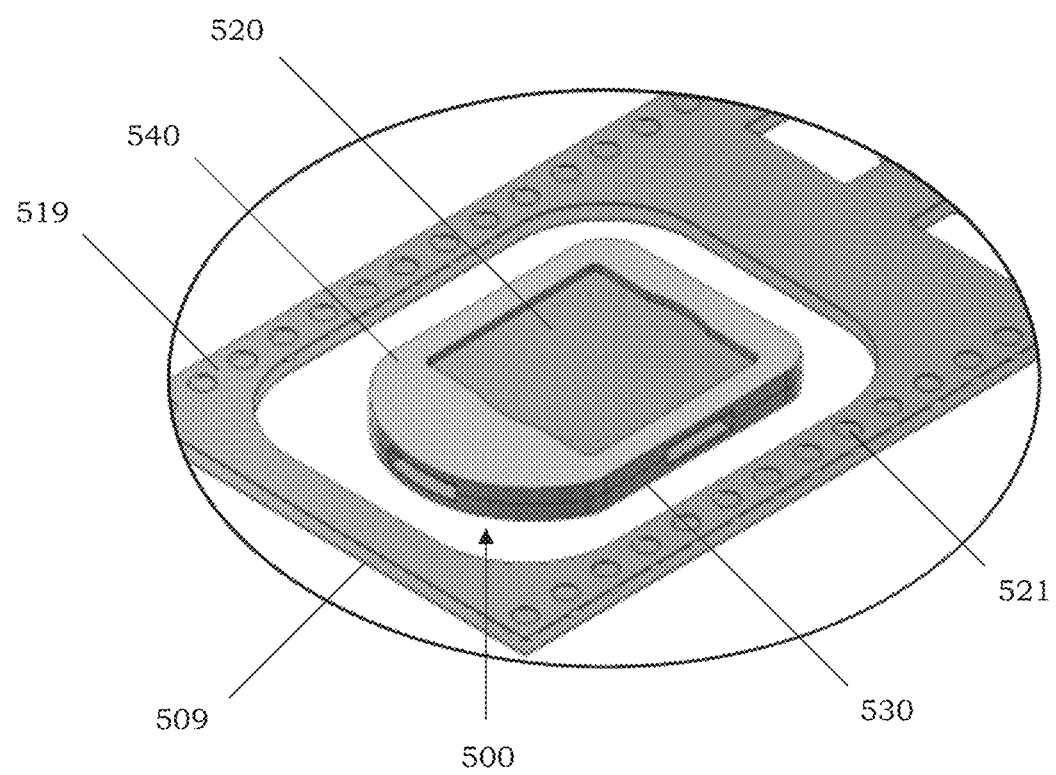

Referring to FIG. 26, the laterally-extending portions of the second sheet 519 and the first sheet 509 are cut (e.g., die cut, laser cut), thereby allowing the second heater 520 and the first heater 510 (e.g., FIG. 17) to be separated therefrom, respectively, along with the capsule 500 as a whole. By using the sheet/web approach discussed herein, a plurality of capsules may be produced relatively consistently and efficiently (e.g., in an automated manner). Although the sheet/web approach was discussed above in connection with the heaters, it should be understood that this methodology may also be applied to the aerosol-forming substrate (e.g., aerosol-forming substrate 760).

Figure 27:
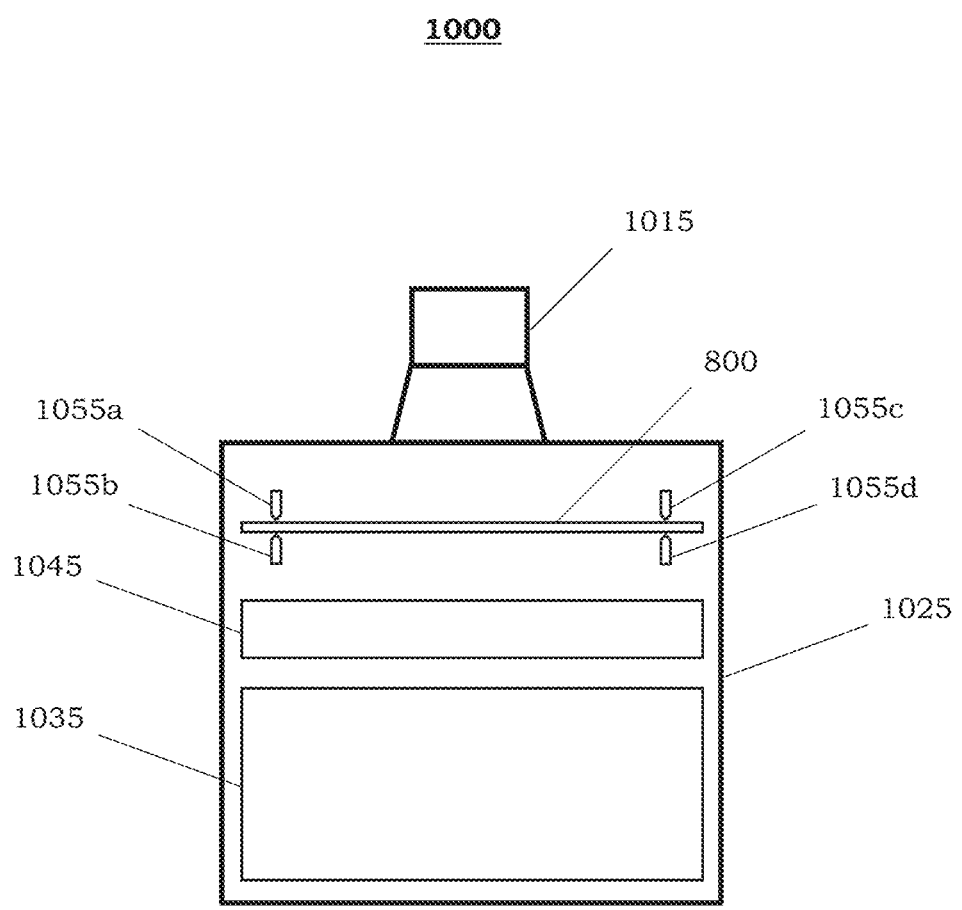
FIG. 27 is a schematic view of an aerosol-generating device according to an example embodiment.

FIG. 27 is a schematic view of an aerosol-generating device according to an example embodiment. Referring to FIG. 27, an aerosol-generating device 1000 (e.g., heat-not-burn aerosol-generating device) may include a mouthpiece 1015 and a device body 1025. A power source 1035 and control circuitry 1045 may be disposed within the device body 1025 of the aerosol-generating device 1000. The aerosol-generating device 1000 is configured to receive a capsule 800, which may be as described in connection with any of the embodiments herein. The aerosol-generating device 1000 may also include a first electrode 1055a, a second electrode 1055b, a third electrode 1055c, and a fourth electrode 1055d configured to electrically contact the capsule 800. In an example embodiment, if the capsule 800 has a structure resembling the capsule 100 of FIG. 1, then the first electrode 1055a and the third electrode 1055c may electrically contact the first heater 110, while the second electrode 1055b and the fourth electrode 1055d may electrically contact the second heater 120. However, in non-limiting embodiments involving a capsule with only one heater, it should be understood that the first electrode 1055a and the third electrode 1055c (or the second electrode 1055b and the fourth electrode 1055d) may be omitted.

When the capsule 800 is inserted into the aerosol-generating device 1000, the control circuitry 1045 may instruct the power source 1035 to supply an electric current to the first electrode 1055a, the second electrode 1055b, the third electrode 1055c, and/or the fourth electrode 1055d. The supply of current from the power source 1035 may be in response to a manual operation (e.g., button-activation) or an automatic operation (e.g., puff-activation). As a result of the current, the capsule 800 may be heated to generate an aerosol.

Additional details of the capsule 800 and the aerosol-generating device 1000, including the mouthpiece 1015, the device body 1025, the power source 1035, the control circuitry 1045, the first electrode 1055a, the second electrode 1055b, the third electrode 1055c, and the fourth electrode 1055d may be found in U.S. application Ser. No.

15/845,501, filed Dec. 18, 2017, titled "VAPORIZING DEVICES AND METHODS FOR DELIVERING A COMPOUND USING THE SAME," the disclosure of which is incorporated herein in its entirety by reference. The capsule, aerosol-forming substrate, and related aspects discussed herein are also described in more detail in U.S. application Ser. No. 16/252,951, filed Jan. 21, 2019, titled "CAPSULE, HEAT-NOT-BURN (HNB) AEROSOL-GENERATING DEVICES, AND METHODS OF GENERATING AN AEROSOL," the disclosure of which is incorporated herein in its entirety by reference.

Figure 28:
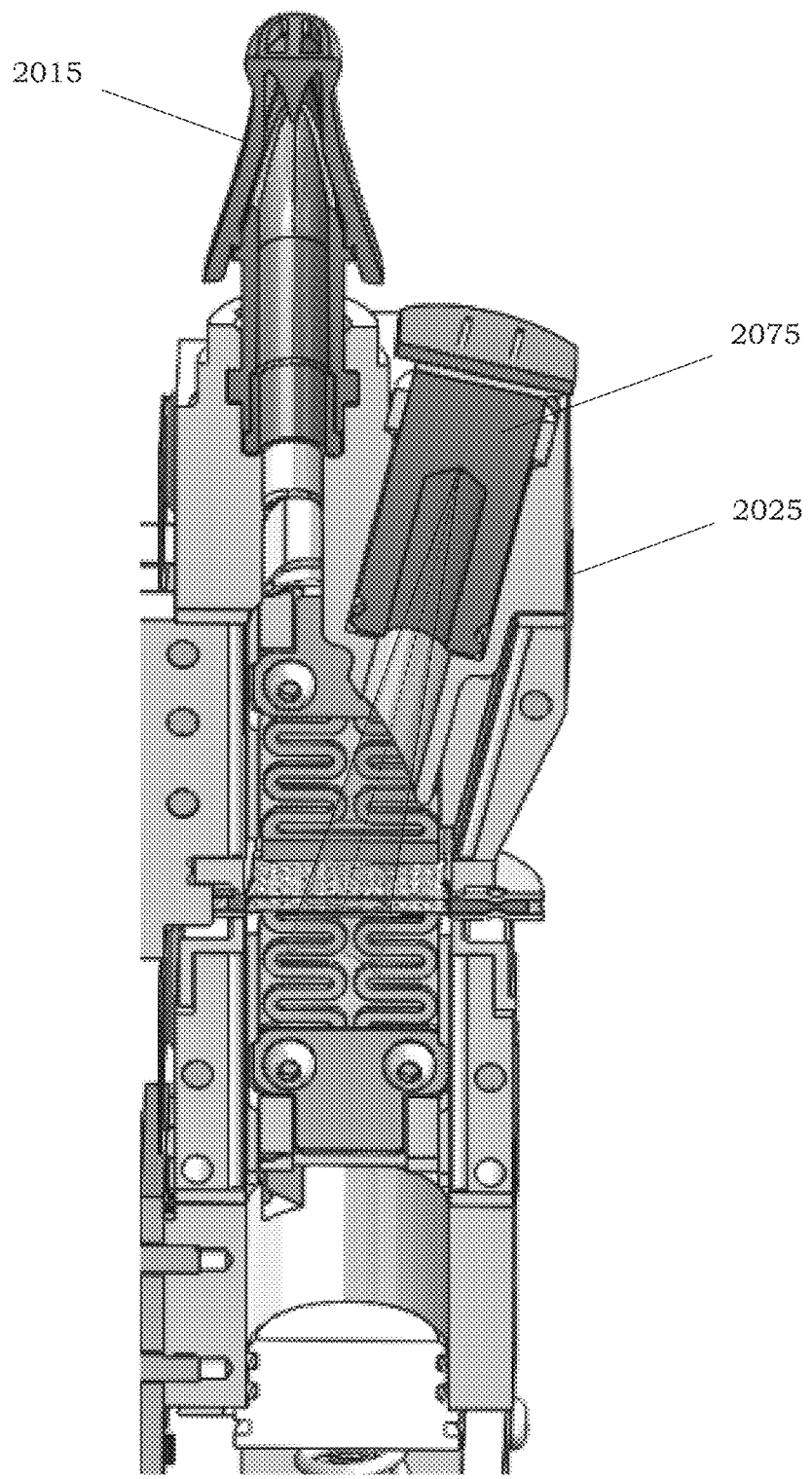
FIG. 28 is a cross-sectional view of another aerosol-generating device according to an example embodiment.

FIG. 28 is a cross-sectional view of another aerosol-generating device according to an example embodiment. Referring to FIG. 28, an aerosol-generating device 2000 (e.g., heat-not-burn aerosol-generating device) may include, inter alia, a mouthpiece 2015 and a device body 2025. It should be understood that the features in connection with the aerosol-generating device 1000 of FIG. 27 may also be applicable to this section and will not be repeated in the interest of brevity. As shown in FIG. 28, a sensor 2075 may be included to measure a temperature of a capsule within the aerosol-generating device 2000. For instance, the sensor 2075 may be an infrared (IR) sensor configured to perform contactless temperature sensing of a capsule. The sensor 2075 may be disposed so as to be downstream from and above a capsule within the device body 2025. In addition, the sensor 2075 may be offset from the aerosol path and oriented at an angle relative to the longitudinal axis of the aerosol-generating device 2000. In an example embodiment, the longitudinal axis may be orthogonal to a plane corresponding to a face of the capsule, and the angle may be 8-20 degrees (e.g., 13-15 degrees) relative to the longitudinal axis. As a result, buildup and deposits from the generated aerosol may be reduced or prevented, thereby enhancing the performance and longevity of the sensor 2075. Additional details of the capsule and the aerosol-generating device, including the sensor and the electrode-movement mechanism may also be found in U.S. application Ser. No. 15/559,308, filed Sep. 18, 2017, titled "VAPORIZER FOR VAPORIZING AN ACTIVE INGREDIENT," the disclosure of which is incorporated herein in its entirety by reference.

Figure 29:
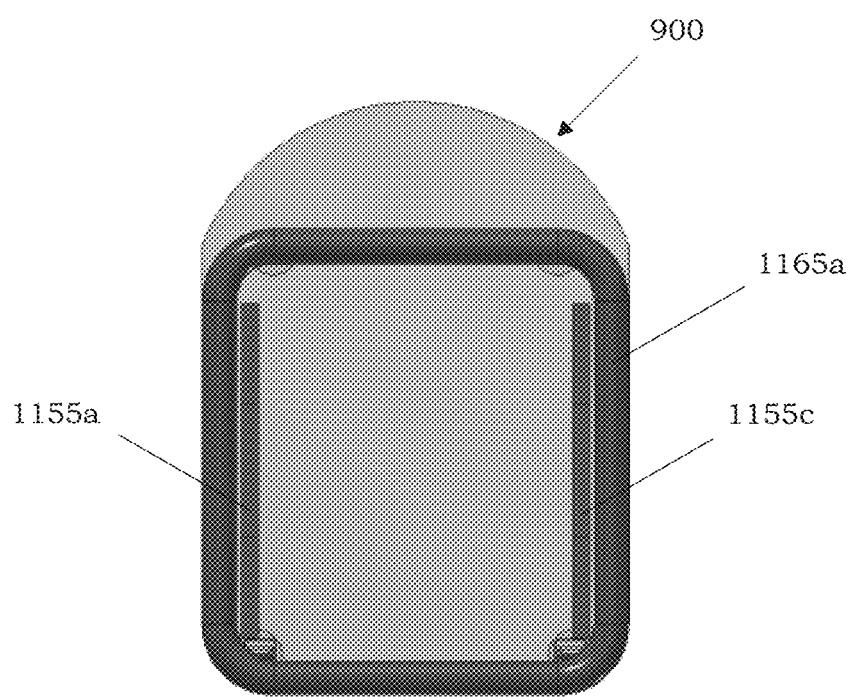
FIG. 29 is a plan view of an arrangement including a capsule engaged by electrodes and seals of an aerosol-generating device according to an example embodiment.
Figure 30:
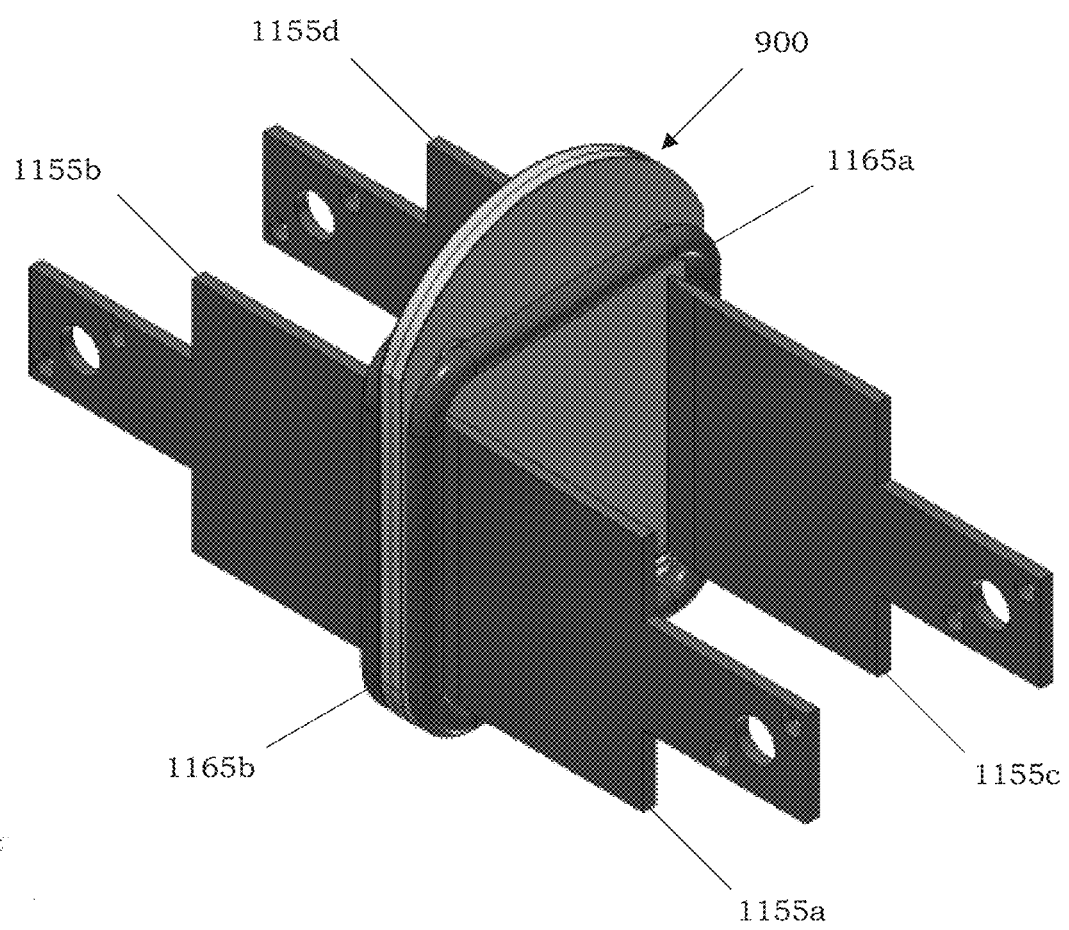
FIG. 30 is a perspective view of the arrangement of FIG. 29.
Figure 31:
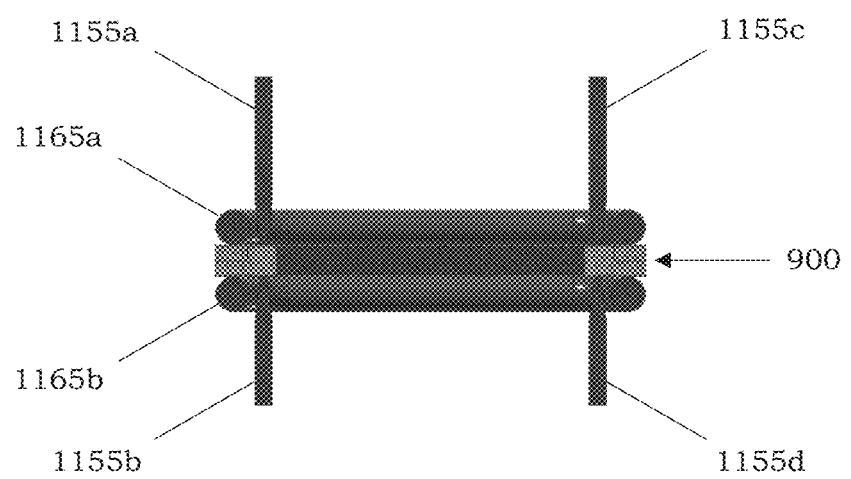
FIG. 31 is a side cross-sectional view of the arrangement of FIG. 29.

FIG. 29 is a plan view of an arrangement including a capsule engaged by electrodes and seals of an aerosol-generating device according to an example embodiment. FIG. 30 is a perspective view of the arrangement of FIG. 29. FIG. 31 is a side cross-sectional view of the arrangement of FIG. 29. Referring to FIGS. 29-31, a capsule 900 within an aerosol-generating device may be engaged by a first seal 1165a and a second seal 1165b. The first seal 1165a may be engaged with a side of the capsule 900 corresponding to a first heater, while the second seal 1165b may be engaged with a side of the capsule 900 corresponding to a second heater (or vice versa). When engaged, the first seal 1165a and the second seal 1165b may be on a periphery of the cavity so as to surround the aerosol-forming substrate disposed therein.

A first electrode 1155a, a second electrode 1155b, a third electrode 1155c, and a fourth electrode 1155d are configured to electrically contact the capsule 900. In an example embodiment, if the capsule 900 has a structure resembling the capsule 100 of FIG. 1, then the first electrode 1155a and the third electrode 1155c may electrically contact the first heater 110, while the second electrode 1155b and the fourth electrode 1155d may electrically contact the second heater 120. However, in non-limiting embodiments involving a capsule with only one heater, it should be understood that the first electrode 1155a and the third electrode 1155c (or the second electrode 1155b and the fourth electrode 1155d) may be omitted.

When engaged with the heaters, the first electrode 1155a and the third electrode 1155c are within the area bounded by the first seal 1165a, while the second electrode 1155b and the fourth electrode 1155d are within the area bounded by the second seal 1165b. The first electrode 1155a and the third electrode 1155c may also be adjacent to opposite sides of the first seal 1165a such that the first heater is pressed against the underlying first frame. Similarly, the second electrode 1155b and the fourth electrode 1155d may be adjacent to opposite sides of the second seal 1165b such that the second heater is pressed against the underlying second frame. In example embodiments involving a third frame, the heaters may be pressed against the underlying third frame by the electrodes.

The first electrode 1155a, the second electrode 1155b, the third electrode 1155c, and the fourth electrode 1155d may be in the form of blades. Additionally, to reduce contact resistance, the first electrode 1155a, the second electrode 1155b, the third electrode 1155c, and the fourth electrode 1155d may be formed of steel and coated with titanium nitride. In an example embodiment, the blades may be straight-edged. Alternatively, the blades may be serrated to enhance an electrical contact in instances where the heaters have an uneven surface (e.g., heaters in the form of a mesh).

The first electrode 1155a, the second electrode 1155b, the third electrode 1155c, and the fourth electrode 1155d may be spring-loaded so as to default to a closed/engaged position. For instance, the first electrode 1155a may be biased towards the second electrode 1155b, while the third electrode 1155c may be biased towards the fourth electrode 1155d. The actuation of the first electrode 1155a, the second electrode 1155b, the third electrode 1155c, and the fourth electrode 1155d to an open/disengaged position may be performed manually. In an example embodiment, a lever may be connected to the first electrode 1155a and the third electrode 1155c such that the first electrode 1155a and the third electrode 1155c are mobile and configured to move together, while the second electrode 1155b and the fourth electrode 1155d are stationary. Conversely, a lever may be connected to the second electrode 1155b and the fourth electrode 1155d such that the second electrode 1155b and the fourth electrode 1155d are mobile and configured to move together, while the first electrode 1155a and the third electrode 1155c are stationary. Alternatively, a first lever may be connected to the first electrode 1155a and the third electrode 1155c, and a second lever may be connected to the second electrode 1155b and the fourth electrode 1155d such that all four of the electrodes are mobile and configured to move together. In such an instance, the first lever and the second lever may be in a criss-cross arrangement so as to undergo a scissor-like movement when actuated, although example embodiments are not limited thereto.

To achieve the open/disengaged position (e.g., for the insertion of the capsule 900), the lever(s) may be pressed to separate the first electrode 1155a and the third electrode 1155c from the second electrode 1155b and the fourth electrode 1155d, respectively. Upon release of the lever(s), the first electrode 1155a, the second electrode 1155b, the third electrode 1155c, and the fourth electrode 1155d may be configured to return to the default closed position by virtue of their spring-loaded arrangement (e.g., so as to engage the capsule 900 inserted within the aerosol-generating device). However, it should be understood that, in some instances, the spring-loaded arrangement(s) may be omitted with regard to the first electrode 1155a, the second electrode 1155b, the third electrode 1155c, and/or the fourth electrode 1155d. In such an instance, manually moving the lever(s) in the opposite direction will achieve the desired movement of the first electrode 1155a, the second electrode 1155b, the third electrode 1155c, and/or the fourth electrode 1155d. In addition, the lever(s) may be configured to require an intentional level of manual force for movement so as to allow the lever(s) to hold their position until further movement is desired.

In another example embodiment, a rack and pinion arrangement may be utilized to achieve the above-discussed open and closed positions for the first electrode 1155a, the second electrode 1155b, the third electrode 1155c, and the fourth electrode 1155d. A rack and pinion arrangement includes a circular gear (pinion) that engages a linear gear (rack) so as to translate a rotational motion of the circular gear into a linear motion of the linear gear (and vice versa). For instance, a linear gear may be connected to the first electrode 1155a and the third electrode 1155c such that the first electrode 1155a and the third electrode 1155c are mobile and configured to move together upon rotation of a corresponding circular gear, while the second electrode 1155b and the fourth electrode 1155d are stationary. Conversely, a linear gear may be connected to the second electrode 1155b and the fourth electrode 1155d such that the second electrode 1155b and the fourth electrode 1155d are mobile and configured to move together upon rotation of a corresponding circular gear, while the first electrode 1155a and the third electrode 1155c are stationary. Alternatively, a first linear gear may be connected to the first electrode 1155a and the third electrode 1155c, and a second linear gear may be connected to the second electrode 1155b and the fourth electrode 1155d such that all four of the electrodes are mobile and configured to move together upon rotation of a corresponding gear or gear assembly. In such an instance, an intermediate circular gear may be provided for one of the first linear gear or the second linear gear to cause the first linear gear and the second linear gear to move in opposite directions (e.g., while in parallel) upon rotation of a primary circular gear. Notably, the primary circular gear may engage the first linear gear directly while engaging the second linear gear indirectly via the intermediate circular gear (or vice versa).

To achieve the open/disengaged position (e.g., for the insertion of the capsule 900), the circular gear(s) may be rotated to cause the linear gear(s) to move away from each other, thereby separating the first electrode 1155a and the third electrode 1155c from the second electrode 1155b and the fourth electrode 1155d, respectively. Upon release of the circular gear(s), the first electrode 1155a, the second electrode 1155b, the third electrode 1155c, and the fourth electrode 1155d may be configured to return to the default closed position by virtue of their spring-loaded arrangement (e.g., so as to engage the capsule 900 inserted within the aerosol-generating device). However, it should be understood that, in some instances, the spring-loaded arrangement(s) may be omitted with regard to the first electrode 1155a, the second electrode 1155b, the third electrode 1155c, and/or the fourth electrode 1155d. In such an instance, manually rotating the circular gear(s) in the opposite direction will achieve the desired linear movement of the first electrode 1155a, the second electrode 1155b, the third electrode 1155c, and/or the fourth electrode 1155d. In addition, the circular gear(s) may be configured to require an intentional level of manually-induced rotational force for movement so as to allow the circular gear(s) to hold their position until further movement is desired.

The first seal 1165a and the second seal 1165b are also configured to transition between an open/disengaged positon (e.g., for insertion of the capsule 900) and a closed/engaged position (e.g., to clamp down and define an air passage through the inserted capsule 900). Although not illustrated, the first seal 1165a and the second seal 1165b may be mounted on (or otherwise be a part of) a clamp structure that is configured undergo the opening and closing movements. The movement of the clamp structure may be as described in connection with the movement of the first electrode 1155a, the second electrode 1155b, the third electrode 1155c, and the fourth electrode 1155d. For instance, the movement of the clamp structure (and, thus, the first seal 1165a and/or the second seal 1165b) may involve the above-discussed lever(s) and/or rack and pinion arrangement. Furthermore, instead of a manual actuation (e.g., of the electrodes and/or seals), an automatic actuation may be implemented such that the pressing of a button (or other electronic control) will effectuate the desired opening or closing movement.

Figure 32:
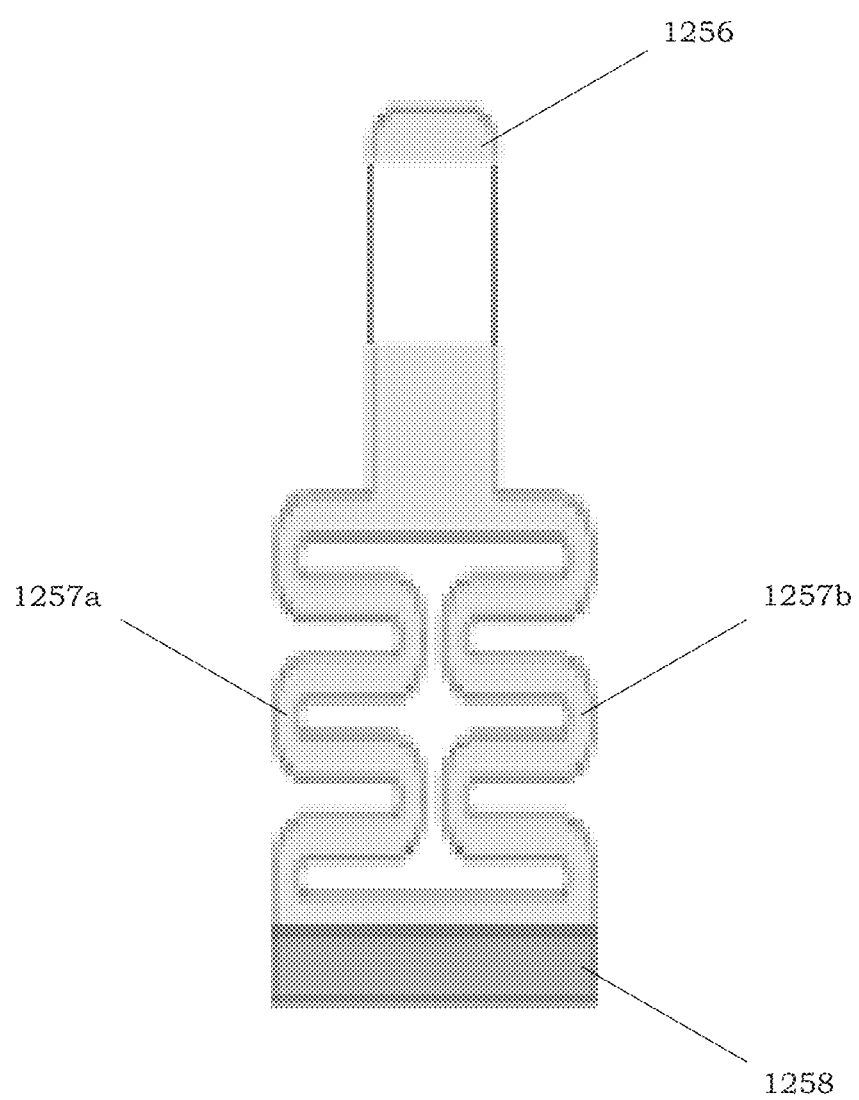
FIG. 32 is a front view of an electrode of an aerosol-generating device according to an example embodiment.

FIG. 32 is a front view of an electrode of an aerosol-generating device according to an example embodiment. Referring to FIG. 32, an electrode 1255 may include a base section 1256, a first resilient section 1257a, a second resilient section 1257b, and a blade section 1258. Each of the first resilient section 1257a and the second resilient section 1257b may have a winding form (e.g., and flexible nature) designed to accommodate inconsistencies of a capsule so as to enhance the electrical contact with its heaters. The blade section 1258 may be straight-edged. Electrodes similar to electrode 1255 are shown (at least in part) in the aerosol-generating device 2000 of FIG. 28.

Figure 33:
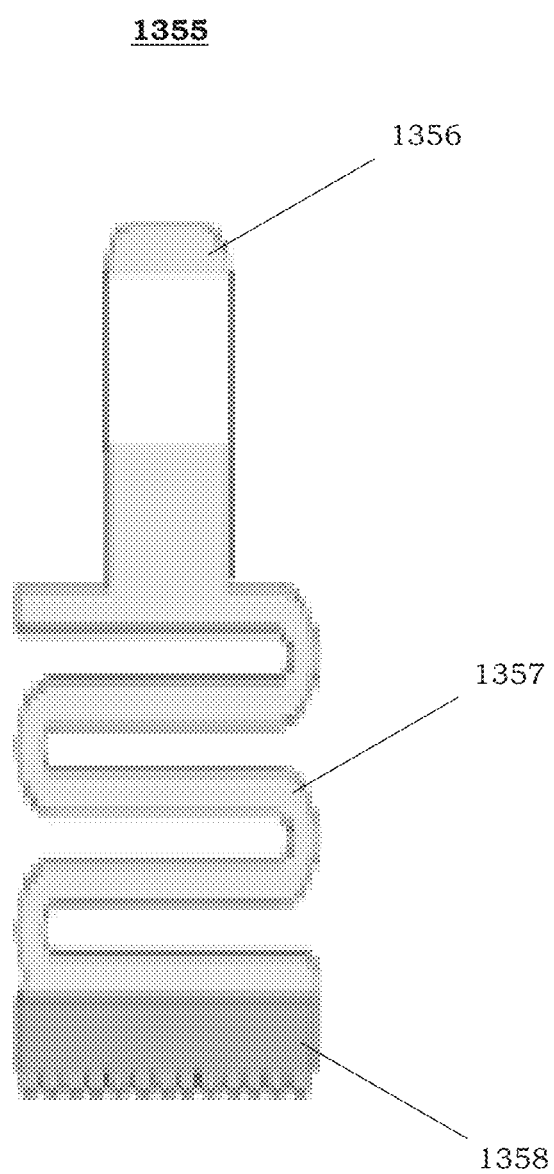
FIG. 33 is a front view of another electrode of an aerosol-generating device according to an example embodiment.

FIG. 33 is a front view of another electrode of an aerosol-generating device according to an example embodiment. Referring to FIG. 33, an electrode 1355 may include a base section 1356, a resilient section 1357, and a blade section 1358. The resilient section 1357 may have a winding form designed to accommodate inconsistencies of a capsule so as to enhance the electrical contact with its heaters. The blade section 1358 may be serrated. Although several examples of the electrodes are illustrated in the figures and discussed herein, it should be understood that other variations are possible. For instance, the electrode 1355 of FIG. 33 may have the first resilient section 1257a and the second resilient section 1257b of FIG. 32. In another instance, the electrode 1355 of FIG. 33 may have the blade section 1258 of FIG. 32.

Figure 34:
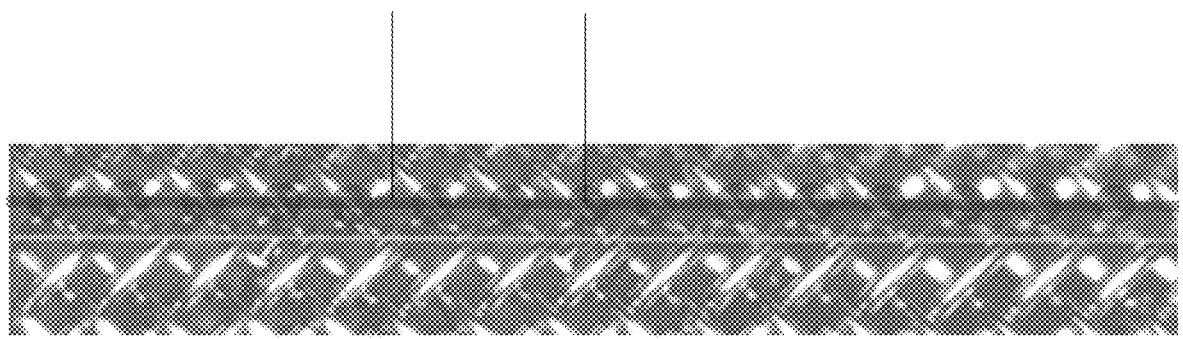
FIG. 34 is an illustration of a connection line and connection points with regard to an engagement of a heater by an electrode according to an example embodiment.

FIG. 34 is an illustration of a connection line and connection points with regard to an engagement of a heater by an electrode according to an example embodiment. Referring to FIG. 34, an electrode may engage a heater 1410 as represented by connection line 1414. Thus, in such an instance, the connection line 1414 is representative of the position of an electrode when engaged with a heater 1410. In addition, when the heater is in a form of a mesh, as illustrated in FIG. 34, the wires of the mesh may be at an angled orientation relative to the connection line 1414. For instance, the wires of the mesh may be at a 35-55 degree angle (e.g., 45 degree angle) relative to the connection line 1414. The connection line 1414 may also be substantially parallel to a side edge of the capsule (e.g., FIG. 29). As a result, the number of connection points 1416 with the electrode may be increased, thus improving the electrical contact and heating.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

The invention claimed is:

1. A capsule for an aerosol-generating device, comprising:

a first frame having a first interior face and a first exterior face, the first frame defining a first opening and including at least one first connector, the at least one first connector including an arm portion and a catch portion, the arm portion being coplanar with the first frame, the catch portion protruding from the first interior face of the first frame;

a first heater secured to the first interior face of the first frame and covering the first opening;

a second frame connected to the first frame, the second frame having a second interior face and a second exterior face, the second frame defining a second opening;

a second heater secured to the second interior face of the second frame and covering the second opening; and an aerosol-forming substrate between the first heater and the second heater.

2. The capsule of claim 1, wherein the first heater and the second heater are in a form of a mesh, a perforated foil, or a combination thereof.

3. The capsule of claim 1, wherein the second frame includes a rim around the second opening so as to define a cavity configured to receive the aerosol-forming substrate.

4. The capsule of claim 3, wherein the rim of the second frame is configured to be seated within the first opening of the first frame.

5. The capsule of claim 1, wherein the at least one first connector includes a ridge extending along an edge of the first interior face of the first frame.

6. The capsule of claim 5, wherein the ridge has a tapered ridgeline.

7. The capsule of claim 1, wherein the at least one first connector includes a projection on the first interior face of the first frame.

8. The capsule of claim 7, wherein the projection has a conical tip.

9. The capsule of claim 1, wherein the second frame defines at least one recess configured to mate with the at least one first connector.

10. The capsule of claim 1, wherein the second frame includes at least one second connector configured to engage with the at least one first connector to form at least one connection such that the first interior face of the first frame is adjacent to the second interior face of the second frame.

11. The capsule of claim 10, wherein the at least one first connector is configured to be in an interlocking arrangement with the at least one second connector.

12. The capsule of claim 10, wherein the at least one first connector is configured to be in a friction fit arrangement with the at least one second connector.

13. The capsule of claim 10, wherein the at least one first connector is configured to be in welded arrangement with the at least one second connector.

14. The capsule of claim 1, further comprising:

a third frame between the first frame and the second frame, the third frame defining a cavity configured to receive the aerosol-forming substrate.

15. The capsule of claim 1, wherein the aerosol-forming substrate includes a plant material.

16. The capsule of claim 15, wherein the plant material includes tobacco.

* * * * *